United States Patent
Ochsner et al.

(10) Patent No.: US 10,392,621 B2
(45) Date of Patent: Aug. 27, 2019

(54) MULTIAPTAMER TARGET DETECTION

(71) Applicant: SomaLogic, Inc., Boulder, CO (US)

(72) Inventors: Urs A. Ochsner, Denver, CO (US);
Louis S. Green, Lafayette, CO (US);
Larry Gold, Boulder, CO (US);
Nebojsa Janjic, Boulder, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

(21) Appl. No.: 15/895,723

(22) Filed: Feb. 13, 2018

(65) Prior Publication Data

US 2018/0187197 A1 Jul. 5, 2018

Related U.S. Application Data

(63) Continuation of application No. 15/023,182, filed as application No. PCT/US2014/057143 on Sep. 24, 2014, now Pat. No. 9,926,566.

(60) Provisional application No. 61/881,629, filed on Sep. 24, 2013.

(51) Int. Cl.
| | | |
|---|---|---|
| *A61K 48/00* | (2006.01) | |
| *C07H 21/02* | (2006.01) | |
| *C07H 21/04* | (2006.01) | |
| *C12N 15/115* | (2010.01) | |
| *C12Q 1/6813* | (2018.01) | |
| *C12N 15/10* | (2006.01) | |

(52) U.S. Cl.
CPC ........ *C12N 15/115* (2013.01); *C12N 15/1048* (2013.01); *C12Q 1/6813* (2013.01); *C12N 2310/16* (2013.01); *C12N 2310/33* (2013.01); *C12N 2320/13* (2013.01); *C12Q 2525/205* (2013.01)

(58) Field of Classification Search
CPC . C12Q 1/6813; C12N 15/115; C12N 2310/06
See application file for complete search history.

(56) References Cited

U.S. PATENT DOCUMENTS

| | | | |
|---|---|---|---|
| 8,895,241 | B2 | 11/2014 | Ochsner |
| 2007/0071744 | A1 | 3/2007 | Munch et al. |
| 2009/0004667 | A1 | 1/2009 | Zichi et al. |
| 2009/0163536 | A1 | 6/2009 | Guiles et al. |
| 2009/0215032 | A1 | 8/2009 | White et al. |
| 2010/0035247 | A1 | 2/2010 | Burton |
| 2010/0317723 | A1 | 12/2010 | Lee et al. |
| 2011/0256535 | A1 | 10/2011 | Dolinger et al. |
| 2011/0262922 | A1 | 10/2011 | Chae et al. |
| 2012/0231467 | A1 | 9/2012 | Ochsner et al. |
| 2013/0034847 | A1 | 2/2013 | Kojic et al. |
| 2013/0085079 | A1 | 4/2013 | Gill et al. |
| 2015/0031585 | A1 | 1/2015 | Ochsner et al. |
| 2015/0125867 | A1 | 5/2015 | Ochsner et al. |

FOREIGN PATENT DOCUMENTS

| | | |
|---|---|---|
| WO | WO 2009/012410 | 1/2009 |
| WO | WO 2009/037264 A2 | 3/2009 |
| WO | WO 2009/037264 A3 | 3/2009 |
| WO | WO 2011/101666 | 8/2011 |
| WO | WO 2012/122540 | 9/2012 |
| WO | WO 2013/102096 | 7/2013 |
| WO | WO 2015/048084 A1 | 4/2015 |

OTHER PUBLICATIONS

Cohen et al. (May 2010) Infect Control Hosp Epidemiol 31(5):431-455 "Clinical Practice Guidelines for *Clostridium difficule* Infection in Adults: 2010 Update by the Society for Healthcare Epidemiology of America (SHEA) and the Infectious Diseases Society of America (IDSA)".
EP Extended Search Report issued in EP 12754934.3 dated Oct. 13, 2014.
EP Extended Search Report issued in EP 14847780.5 dated Apr. 20, 2017.
Gold et al. (Dec. 2010) PLoS ONE 5(12), p. e15004, "Aptamer-Based Multiplexed Proteomic Technology for Biomarkers Discovery".
Gong et al. (Jun. 8, 2012) "Selection strategy to generate aptamer pairs that bind to distinct sites on protein targets," Anal Chem., 84(12):5365-5371.
Hicke, B.J. and Stephens, A. W., "Escort aptamers: a delivery service for diagnostics and therapy", J. Clin. Invest. 106(8): 923-928 (2000).
International Preliminary Report on Patentability dated Sep. 10, 2013 in PCT/US2012/028632.
International Search Report and Written Opinion dated Aug. 14, 2012 in PCT/US2012/028632.
International Search Report and Written Opinion dated Dec. 24, 2014 in PCT/US2014/057143.
Lowy et al. (Jan. 2010) N Engl J Med 362(3):195-207 "Treatment with Monoclonal Antibodies against *Clostridium difficile* Toxins".
Ochsner et al. (2011) 111th General Meeting—American Society for Microbiology "Selection and Characterization of Slow Off-rate Modified Aptamers for Clostridium difficile Toxins A/B and Binary Toxin Diagnostic Tests".
Ochsner et al. (Mar. 2014) BioTechniques 56(3):125-133, "Systematic selection of modified aptamer pairs for diagnostic sandwich assays".
Ochsner et al. (May 2013) Diagnostic Microbiology and Infectious Disease 76(3):278-285 "Detection of *Clostridium difficile* toxins A, B and binary toxin with slow off-rate modified aptamers".

*Primary Examiner* — Amy H Bowman
(74) *Attorney, Agent, or Firm* — Adsero IP

(57) ABSTRACT

Described herein are compositions comprising a first aptamer, second aptamer and a target that are capable of forming a ternary complex, and wherein the first aptamer and the second aptamer comprise C-5 pyrimidine modification schemes that are different, and methods of making and using such compositions.

35 Claims, 9 Drawing Sheets
Specification includes a Sequence Listing.

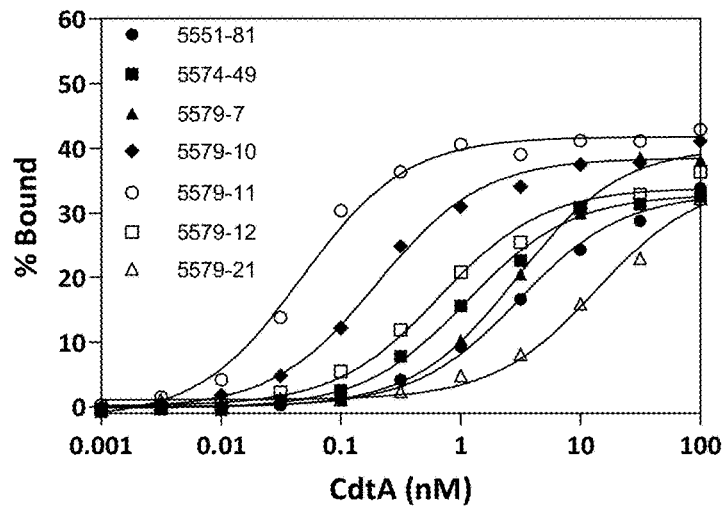
FIG. 1C
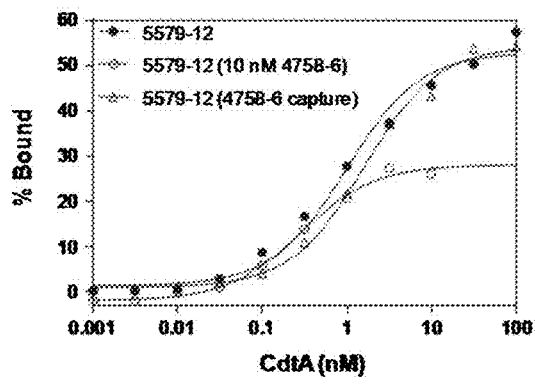 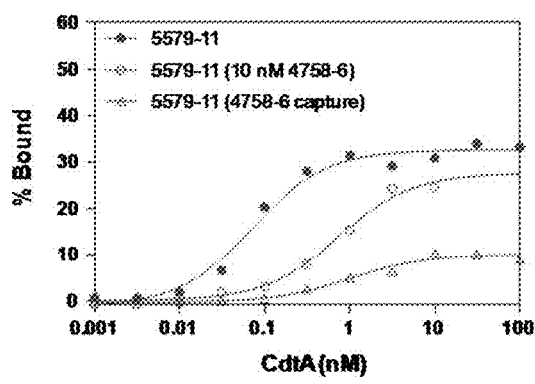
FIG. 1D
FIG. 1E

FIG. 2D
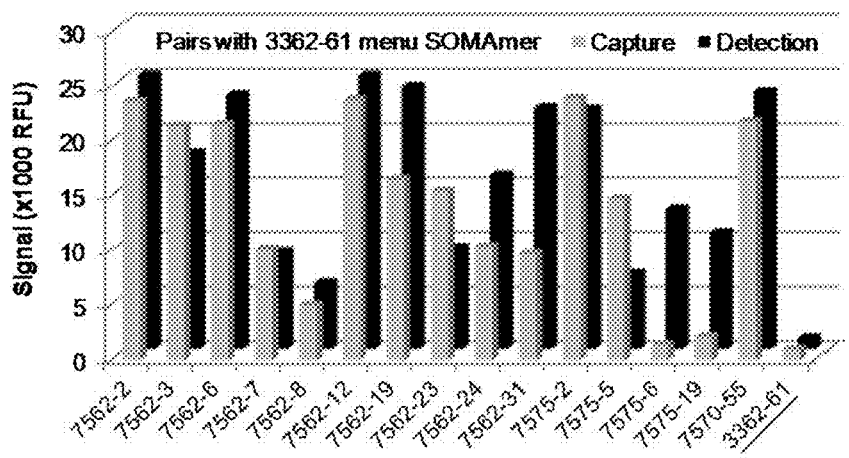
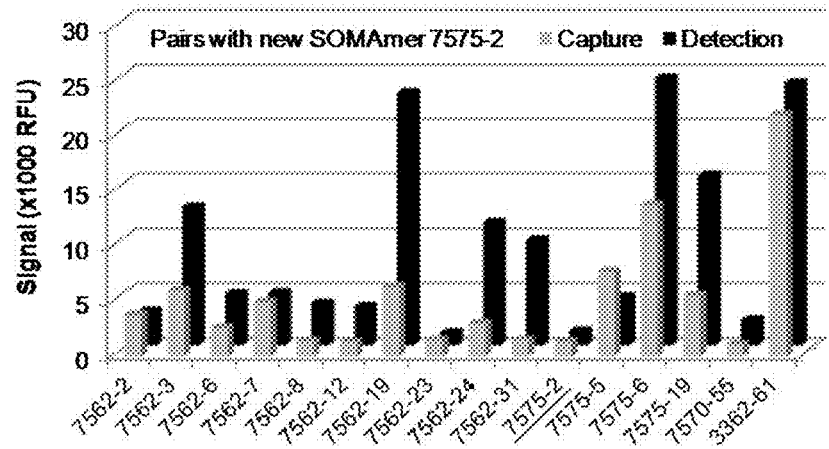
FIG. 2E

SEQUENCE LISTING

<160> NUMBER OF SEQ ID NOS: 4

<210> SEQ ID NO 1
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: 5-[N-(3-indole-2-ethyl)-carboxyamide]-2'-
      deoxyuridine
<220> FEATURE:
<221> NAME/KEY: misc_feature
<222> LOCATION: (12)..(13)
<223> OTHER INFORMATION: 5-[N-(3-indole-2-ethyl)-carboxyamide]-2'-
      deoxyuridine
<220> FEATURE:
<221> NAME/KEY: misc_feature
<222> LOCATION: (15)..(15)
<223> OTHER INFORMATION: 5-[N-(3-indole-2-ethyl)-carboxyamide]-2'-
      deoxyuridine
<220> FEATURE:
<221> NAME/KEY: misc_feature
<222> LOCATION: (20)..(20)
<223> OTHER INFORMATION: 5-[N-(3-indole-2-ethyl)-carboxyamide]-2'-
      deoxyuridine
<220> FEATURE:
<221> NAME/KEY: misc_feature
<222> LOCATION: (23)..(23)
<223> OTHER INFORMATION: 5-[N-(3-indole-2-ethyl)-carboxyamide]-2'-
      deoxyuridine
<220> FEATURE:
<221> NAME/KEY: misc_feature
<222> LOCATION: (25)..(25)
<223> OTHER INFORMATION: 5-[N-(3-indole-2-ethyl)-carboxyamide]-2'-
      deoxyuridine
<220> FEATURE:
<221> NAME/KEY: misc_feature
<222> LOCATION: (30)..(30)
<223> OTHER INFORMATION: 5-[N-(3-indole-2-ethyl)-carboxyamide]-2'-
      deoxyuridine

<400> SEQUENCE: 1
gaagacnnna anncngacan ggngnccaan ggcgcgcgag                            40

<210> SEQ ID NO 2
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(5)
<223> OTHER INFORMATION: 5-[N-(2-naphthylmethyl)carboxyamide]-2'-
      deoxyuridine
<220> FEATURE:
<221> NAME/KEY: misc_feature
<222> LOCATION: (7)..(8)
<223> OTHER INFORMATION: 5-[N-(2-naphthylmethyl)carboxyamide]-2'-
      deoxyuridine

<400> SEQUENCE: 2
gaanngnncc g                                                          11

<210> SEQ ID NO 3
<211> LENGTH: 15
<212> TYPE: DNA
<213> ORGANISM: Artificial Sequence
<220> FEATURE:
<223> OTHER INFORMATION: Synthetic
<220> FEATURE:

```
<221> NAME/KEY: misc_feature
<222> LOCATION: (4)..(5)
<223> OTHER INFORMATION: 5-[N-(2-naphthylmethyl)carboxyamide]-2'-
      deoxyuridine
<220> FEATURE:
<221> NAME/KEY: misc_feature
<222> LOCATION: (11)..(12)
<223> OTHER INFORMATION: 5-[N-(2-naphthylmethyl)carboxyamide]-2'-
      deoxyuridine

<400> SEQUENCE: 3
gganngcagg nnccc                                                     15

<210> SEQ ID NO 4
<211> LENGTH: 10
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: 5-[N-(2-naphthylmethyl)carboxyamide]-2'-
      deoxyuridine
<220> FEATURE:
<221> NAME/KEY: misc_feature
<222> LOCATION: (6)..(6)
<223> OTHER INFORMATION: 5-[N-(2-naphthylmethyl)carboxyamide]-2'-
      deoxyuridine
<220> FEATURE:
<221> NAME/KEY: misc_feature
<222> LOCATION: (8)..(8)
<223> OTHER INFORMATION: 5-[N-(2-naphthylmethyl)carboxyamide]-2'-
      deoxyuridine

<400> SEQUENCE: 4 gaancnanac                                                           10
```

MULTIAPTAMER TARGET DETECTION

RELATED APPLICATIONS

This application is a continuation of U.S. application Ser. No. 15/023,182, filed Mar. 18, 2016, which is a 35 U.S.C. § 371 national phase application of PCT/US2014/057143 (WO2015/048084), filed on Sep. 24, 2014, which application claims priority under 35 U.S.C. § 119(e) to U.S. provisional application Ser. No. 61/881,629, filed on Sep. 24, 2013. Each of these references is incorporated herein by reference in its entirety.

FIELD

The present disclosure relates generally to the field of nucleic acid ligands, and more specifically, to aptamer pair based target detection; compositions comprising aptamer pairs and a target; and methods of making and using the same.

Incorporated by reference herein in its entirety is the Sequence Listing entitled "Sequence_Listing_Amended_ST25.txt", created Jan. 11, 2017, size of 3 kilobytes.

BACKGROUND

Protein diagnostics have a wide array of clinical application and are useful in determining proteomic signatures or disease-specific biomarkers. These diagnostics typically require pairs of analyte-specific reagents for capture and detection of the desired target (e.g., protein). Antibodies have been widely used as diagnostic reagents; however they can be difficult to procure in adequate quality and quantity, and allow only limited multiplexing when testing multiple targets. Further, they are limited in arrays for multiplexed or high-content proteomic applications due to their inherent cross-reactivity and non-universal assay conditions.

In contrast to antibodies, nucleic acid-based ligands have several advantages over antibodies including low molecular weight, thermal and desiccation stability, reversible renaturation, ease of manufacturing, and lower cost. However, only few examples of analytes bound by two different aptamers exist to date. As one example, separate DNA aptamers to the fibrinogen-recognition and heparin-binding exosites of thrombin have been described, and both of these aptamers, TBA1 (15-mer) and TBA2 (29-mer), consist of G-quartet motifs that bind to discrete electropositive surfaces on thrombin. Sandwich assays with TBA1 and TBA2 have been developed for potential thrombin monitoring, including aptamer microarrays and fluorescence sensing platforms. Another example is integrin $\alpha_V\beta_3$, for which RNA aptamers to $\alpha_V$ or $\beta_3$ subunits have been generated via successive selections with $\alpha_V\beta_3$ or $\alpha_{IIb}\beta_3$. Aptamer pairs to TATA binding protein (TBP), prion protein (PrP), and VEGF-165 have also been reported. The limited number of aptamer pairs for detecting protein targets is likely the result of the propensity of aptamers to bind to predominantly cationic epitopes which drives the best ligands to common surfaces. Thus, special selection methods have generally been required to force the selection toward non-overlapping epitopes.

Therefore, there continues to be a need for alternative composition and methods for improved, cost-effective and efficient ways to detect target proteins. The present disclosure meets such needs by providing novel combinations of slow off-rate aptamer (SOMAmer) reagent pairs for protein detection that comprise deoxyuridine residues modified at their 5-position, which both expands the range of protein targets and improves the binding properties compared to conventional aptamers.

SUMMARY

The present disclosure describes a composition comprising a first aptamer, second aptamer and a target, wherein the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are different; and wherein the first aptamer, second aptamer and the target are capable of forming a ternary complex.

In another aspect of the disclosure, the first aptamer has binding affinity for the target and not the second aptamer.

In another aspect, the second aptamer has binding affinity for the target and not the first aptamer.

In another aspect, the second aptamer has binding affinity for a complex formed by the association of the first aptamer with the target.

In another aspect, the first aptamer binding region of the target and the second aptamer binding region of the target are different regions. In a related aspect, the first aptamer and the second aptamer have non-competing binding sites on the target.

In another aspect, the first aptamer and the second aptamer, independently, comprise RNA, DNA or a combination thereof.

In another aspect, the C-5 modified pyrimidine is selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-[N-(phenyl-3-propyl)carboxamide]-2'-deoxyuridine (PPdU), 5-[N-(2-thiophene-methyl)carboxamide]-2'-deoxyuridine (ThdU) (also referred to as 5-(N-thiophenylmethylcarboxyamide)-2'-deoxyuridine), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-[N-(1-naphthylethyl)carboxyamide]-2'-deoxyuridine (NEdU), 5-[N-(2-naphthylethyl)carboxyamide]-2'-deoxyuridine 2NEdU), 5-[N-(4-fluorobenzyl)carboxyamide]-2'-deoxyuridine FBndU), 5-[N-(4-hydroxyphenyl-2-ethyl)carboxamide]-2'-deoxyuridine (TyrdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine, 5-[N-(3-benzo[b]thiophene-2-ethyl)carboxyamide]-2'-deoxyuridine (BTdU), 5-[N-(3-benzo[a]furan-2-ethyl)carboxyamide]-2'-deoxyuridine (BFdU), 5-[N-(3,4-methylenedioxybenzyl)carboxamide]-2'-deoxyuridine (MBndU), 5-[N—((R)-2-tetrahydrofurylmethyl)carboxamide]-2'-deoxyuridine (RTHdU), 5-[N—((S)-2-tetrahydrofurylmethyl)carboxamide]-2'-deoxyuridine (STHFdU), 5-(N-2-imidazolylethylcarboxamide)-2'-deoxyuridine (ImiddU), 5-[N-(1-morpholino-2-ethyl)carboxamide]-2'-deoxyuridine (MOEdU), and a combination thereof.

In another related aspect, the first C-5 pyrimidine modification scheme comprises a 5-(N-benzylcarboxyamide)-2'-deoxyuridine (BndU).

In another aspect, each uracil or thymine of the first aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine. In a related aspect, each uracil or thymine of the first aptamer is a 5-(N-benzylcarboxyamide)-2'-deoxyuridine (BndU).

In another aspect, the second C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-[1-naphthylmethyl]carboxyamide)-2'-deoxyuridine (NapdU), 5-(N-[2-naphthylmethyl]carboxyamide)-2'-deoxyuridine (2-NapdU), 5-(N-naphthylmethyl-carboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the second C-5 pyrimidine modification scheme comprises a C-5 modified pyrimidine selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the second C-5 pyrimidine modification scheme comprises a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

In another aspect, each uracil or thymine of the second aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine.

In a related aspect, each uracil or thymine of the second aptamer is a 5-(N-benzylcarboxyamide)-2'-deoxyuridine (BndU).

In another aspect, the percent GC content of the first aptamer and second aptamer are, independently, from about 37% to about 58% (or about 37%, 38%, 39%, 40%, 41%, 42%, 43%, 44%, 45%, 46%, 47%, 48%, 49%, 50%, 51%, 52%, 53%, 54%, 55%, 56%, 57% or 58%).

In another aspect, the first aptamer comprises from about 9 to about 16 (or about 9, 10, 11, 12, 13, 14, 15, or 16) C-5 modified pyrimidines.

In another aspect, the second aptamer comprises from about 5 to about 15 C-modified pyrimidines (or about 5, 6, 7, 8, 9, 10, 11, 12, 13, 14 or 15).

In another aspect, the first aptamer and the second aptamer, independently, are each from about 20 to 100 nucleotides in length (or from 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In a related aspect, the first aptamer and the second aptamer, independently, are from about 40 to about 100 nucleotides in length (or from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the first aptamer and/or the second aptamer further comprise a detectable moiety. In a related aspect, the detectable moiety is selected from the group consisting of a dye, a quantum dot, a radiolabel, an electrochemical functional group, an enzyme, an enzyme substrate, a ligand and a receptor.

In another aspect, the target comprises a protein or a peptide. In a related aspect, the target is a protein selected from the group consisting ANGPT2, TSP2, CRDL1, MATN2, GPVI, ESAM, C7, PLG, MMP-12, NPS-PLA2 and CdtA.

In another aspect, the dissociation constant ($K_d$) for the ternary complex is at least 0.02 nM, or from about 0.01 nM to about 10 nM, or from about 0.02 nM to about 6 nM (or from about 0.02, 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9 or 6 nM) or from about 0.02 nM to about 3 nM (or from 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 nM).

The present disclosure further describes a method for detecting a target in a sample, the method comprising: contacting the sample with a first aptamer to form a mixture, wherein the first aptamer is capable of binding to the target to form a first complex; incubating the mixture under conditions that allow for the first complex to form; contacting the mixture with a second aptamer, wherein the second aptamer is capable of binding the first complex to form a second complex; incubating the mixture under conditions that allow for the second complex to form; detecting for the presence or absence of the first aptamer, the second aptamer, the target, the first complex or the second complex in the mixture, wherein the presence of the first aptamer, the second aptamer, the target, the first complex or the second complex indicates that the target is present in the sample; and wherein, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are different.

In one aspect, the present disclosure further provides that any of the methods disclosed herein may optionally be subject to or comprise a kinetic challenge. In another aspect, the methods described herein further comprise the addition of a competitor molecule, a dilution step or one or more washes to improve the binding affinity of the aptamer with the target. In a related aspect, the competitor molecule is selected from the group consisting of an oligonucleotide, heparin, herring sperm DNA, salmon sperm DNA, dextran sulfate, polyanion, abasic phosphodiester polymer, dNTP, and pyrophosphate. In another aspect, the kinetic challenge comprises diluting the mixture containing any of the complexes as described herein, and incubating the mixture containing the aptamer affinity complex for a time selected from the group consisting of greater than or equal to 30 seconds, 1 minute, 2 minutes, 3 minutes, 4 minutes, 5 minutes, 10 minutes, 30 minutes, and 60 minutes. In another aspect, the kinetic challenge comprises diluting the mixture containing the aptamer affinity complex and incubating the mixture containing the aptamer affinity complex for a time such that the ratio of the measured level of aptamer affinity complex to the measured level of the non-specific complex is increased.

In another aspect, the method for detecting a target in a sample comprises contacting the sample with the first and second aptamers simultaneously, incubating the mixture under conditions that allow the formation of a complex comprising the target and first and second aptamers, and detecting for the presence or absence of the first aptamer, the second aptamer, the target or the complex in the mixture, wherein the presence of the first aptamer, the second aptamer or the complex indicates that the target is present in the sample.

In another aspect, the first and second aptamers can both independently form a complex with the target. Specifically, the second aptamer can form a complex with the target alone as well as with the complex between the first aptamer and the target.

In another aspect, the first aptamer has binding affinity for the target and not the second aptamer.

In another aspect, the second aptamer has binding affinity for the target and not the first aptamer.

In another aspect, the second aptamer has binding affinity for the first complex.

In another aspect, the first aptamer binding region of the target and the second aptamer binding region of the target are different regions. In a related aspect, the first aptamer and the second aptamer have non-competing binding sites on the target.

In another aspect, the first aptamer and the second aptamer, independently, comprise RNA, DNA or a combination thereof.

In another aspect, the first C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the first C-5 pyrimidine modification scheme comprises a C-5 modified pyrimidine selected from the group consisting of a 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the first C-5 pyrimidine modification scheme comprises a C-5 modified pyrimidine selected from the group consisting of a 5-(N-benzylcarboxyamide)-2'-deoxyuridine (BndU), a 5-(N-tryptaminocarboxyamide)-2'-deoxyuridine (TrpdU) and a combination thereof. In another related aspect, the first C-5 pyrimidine modification scheme comprises a 5-(N-benzylcarboxyamide)-2'-deoxyuridine (BndU).

In another aspect, each uracil or thymine of the first aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N- naphthylmethylcarboxyamide)-2'-fluorouridine and a 5-(N-[1-(2,3-dihydroxypropyl)]carboxyamide)-2'-deoxyuridine. In a related aspect, each uracil or thymine of the first aptamer is a 5-(N-benzylcarboxyamide)-2'-deoxyuridine (BndU).

In another aspect, the second C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the second C-5 pyrimidine modification scheme comprises a C-5 modified pyrimidine selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the second C-5 pyrimidine modification scheme comprises a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

In another aspect, each uracil or thymine of the second aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine. In a related aspect, each uracil or thymine of the second aptamer is a 5-(N-benzylcarboxyamide)-2'-deoxyuridine (BndU).

In another aspect, the first aptamer and the second aptamer, independently, are each from 20 to 100 nucleotides in length (or from 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length). In a related aspect, the first aptamer and the second aptamer, independently, are from about 40 to about 100 nucleotides in length (or from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the first aptamer and/or the second aptamer further comprise a detectable moiety. In a related aspect, the detectable moiety is selected from the group consisting of a dye, a quantum dot, a radiolabel, an electrochemical functional group, an enzyme, an enzyme substrate, a ligand and a receptor.

In another aspect, the target comprises a protein or a peptide. In a related aspect, the target is a protein selected from the group consisting ANGPT2, TSP2, CRDL1, MATN2, GPVI, ESAM, C7, PLG, MMP-12, NPS-PLA2 and CdtA.

In another aspect, the dissociation constant ($K_d$) for the second complex is at least 0.02 nM, or from about 0.01 nM to about 10 nM, or from about 0.02 nM to about 6 nM (or from about 0.02, 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9 or 6 nM) or from about 0.02 nM to about 3 nM (or from 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 nM).

In another aspect, the dissociation constant ($K_d$) for the first complex is from about 0.04 nM to about 5 nM (or from 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 nM), or from about 0.04 nM to about 4.8 nM (or from 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7 or 4.8).

In another aspect, the dissociation constant ($K_d$) for the second aptamer and the target is from about 0.03 nM to about 14 nM (or from 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.2, 10.4, 10.6, 10.8, 11, 11.2, 11.4, 11.6, 11.8, 12, 12.2, 12.4, 12.6, 12.8, 13, 13.2, 13.4, 13.6, 13.8 or 14 nM).

The present disclosure further describes a method comprising contacting a target with a first aptamer to form a mixture, wherein the first aptamer is capable of binding the target to form a first complex; incubating the mixture under conditions that allow for the first complex to form; contacting the mixture with a second aptamer, wherein the second aptamer is capable of binding the target to form a second complex; incubating the mixture under conditions that allow for the second complex to form; detecting for the presence or absence of the first aptamer and the second aptamer in the mixture, wherein the presence of both the first aptamer and second aptamer in the mixture indicates that the binding of the first aptamer to the target and the binding of the second aptamer to the target is non-competitive; and wherein, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are different.

In another aspect, the first aptamer has binding affinity for the target and not the second aptamer.

In another aspect, the second aptamer has binding affinity for the target and not the first aptamer.

In another aspect, the second aptamer has binding affinity for the first complex.

In another aspect, the first aptamer binding region of the target and the second aptamer binding region of the target are different regions. In a related aspect, the first aptamer and the second aptamer have non-competing binding sites on the target.

In another aspect, the first aptamer and the second aptamer, independently, comprise RNA, DNA or a combination thereof.

In another aspect, the first C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the first C-5 pyrimidine modification scheme comprises a C-5 modified pyrimidine selected from the group consisting of a 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the first C-5 pyrimidine modification scheme comprises a C-5 modified pyrimidine selected from the group consisting of a 5-(N-benzylcarboxyamide)-2'-deoxyuridine (BndU), a 5-(N-tryptaminocarboxyamide)-2'-deoxyuridine (TrpdU) and a combination thereof. In another related aspect, the first C-5 pyrimidine modification scheme comprises a 5-(N-benzylcarboxyamide)-2'-deoxyuridine (BndU).

In another aspect, each uracil or thymine of the first aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine.

In a related aspect, each uracil or thymine of the first aptamer is a 5-(N-benzylcarboxyamide)-2'-deoxyuridine (BndU).

In another aspect, the second C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the second C-5 pyrimidine modification scheme comprises a C-5 modified pyrimidine selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the second C-5 pyrimidine modification scheme comprises a C-5 modified pyrimidine selected from the group consisting of 5-(N-tryptaminocarboxyamide)-2'-deoxyuridine (TrpdU), a 5-(N-naphthylmethylcarboxyamide)-2'-deoxyuridine (NapdU) and a combination thereof.

In another aspect, each uracil or thymine of the second aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3- trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine.

In a related aspect, each uracil or thymine of the second aptamer is a 5-(N-benzylcarboxyamide)-2'-deoxyuridine (BndU).

In another aspect, the first aptamer and the second aptamer, independently, are each from 20 to 100 nucleotides in length (or from 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length). In a related aspect, the first aptamer and the second aptamer, independently, are from about 40 to about 100 nucleotides in length (or from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the first aptamer and/or the second aptamer further comprise a detectable moiety. In a related aspect, the detectable moiety is selected from the group consisting of a dye, a quantum dot, a radiolabel, an electrochemical functional group, an enzyme, an enzyme substrate, a ligand and a receptor.

In another aspect, the target comprises a protein or a peptide. In a related aspect, the target is a protein selected from the group consisting ANGPT2, TSP2, CRDL1, MATN2, GPVI, ESAM, C7, PLG, MMP-12, NPS-PLA2 and CdtA.

In another aspect, the dissociation constant ($K_d$) for the second complex is at least 0.02 nM, or from about 0.01 nM to about 10 nM, or from about 0.02 nM to about 6 nM (or from about 0.02, 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9 or 6 nM) or from about 0.02 nM to about 3 nM (or from 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 nM).

In another aspect, the dissociation constant ($K_d$) for the first complex is from about 0.04 nM to about 5 nM (or from 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or 5 nM), or from about 0.04 nM to about 4.8 nM (or from 0.04, 0.06, 0.08, 0.1, 0.15, 0.2, 0.25, 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7 or 4.8).

In another aspect, the dissociation constant ($K_d$) for the second aptamer and the target is from about 0.03 nM to about 14 nM (or from 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.2, 10.4, 10.6, 10.8, 11, 11.2, 11.4, 11.6, 11.8, 12, 12.2, 12.4, 12.6, 12.8, 13, 13.2, 13.4, 13.6, 13.8 or 14 nM).

The present disclosure further provides a composition comprising a first aptamer and/or a second aptamer and a target protein, wherein the first aptamer and/or a second aptamer and the target protein are bound by a non-covalent interaction.

The foregoing and other objects, features, and advantages of the disclosure will become more apparent from the following detailed description, which proceeds with reference to the accompanying figures.

BRIEF DESCRIPTION OF THE DRAWINGS

FIG. 1A shows a free target used in a first SELEX (or 1st SELEX) with a modified random ssDNA library to isolate a set of aptamers, having 5' and 3' fixed regions that can be screened directly for pairs of non-competing clones. Representative chemical modifications that may be used within the 40 nucleotide random region of each aptamer are provided (e.g., abbreviated as Bn, Nap, Trp, PE, Try and 2Nap). If no pairs are present, the aptamer with the best binding properties is allowed to form a complex with the target, which is then used in a second SELEX (or 2nd SELEX) with a different modified library. The new aptamer clones are then screened for paired sandwich binding to the target. FIG. 1C shows equilibrium binding of aptamers with CdtA protein. Clones 5551-81 and 5574-49 were obtained in SELEX with free CdtA, 5579-7 through 5579-21 with CdtA-4758-6 complex in a second SELEX. The maximum bound fraction (binding plateau) in this assay is influenced by the retention efficiency of the target-aptamer complexes on Zorbax and the fraction of binding-competent aptamers. FIGS. 1D and 1E show a CdtA binding assay with radiolabeled 5579-12 (FIG. 1D) or 5579-11 (FIG. 1E) in the absence or presence of a 100-fold excess (10 nM) unlabeled competitor aptamer 4758-6 that was previously generated for CdtA. Binding was also measured using CdtA and biotinylated 4758-6 as a capture agent that had been pre-immobilized on streptavidin beads.

FIGS. 2D and 2E show the evaluation of 16 CRDL1 aptamers as capture agents or detection agents) in the Luminex sandwich screening assay with SOMAmer 3362-61 which was the sequence used to form the complex with CRDL1 during SELEX (FIG. 2D) or with SOMAmer 7575-2 which was one of the new sequences (FIG. 2E). Controls included assays where the same SOMAmer was used for capture and detection (underlined).

DETAILED DESCRIPTION

I. Terms and Methods

Figure 1A:
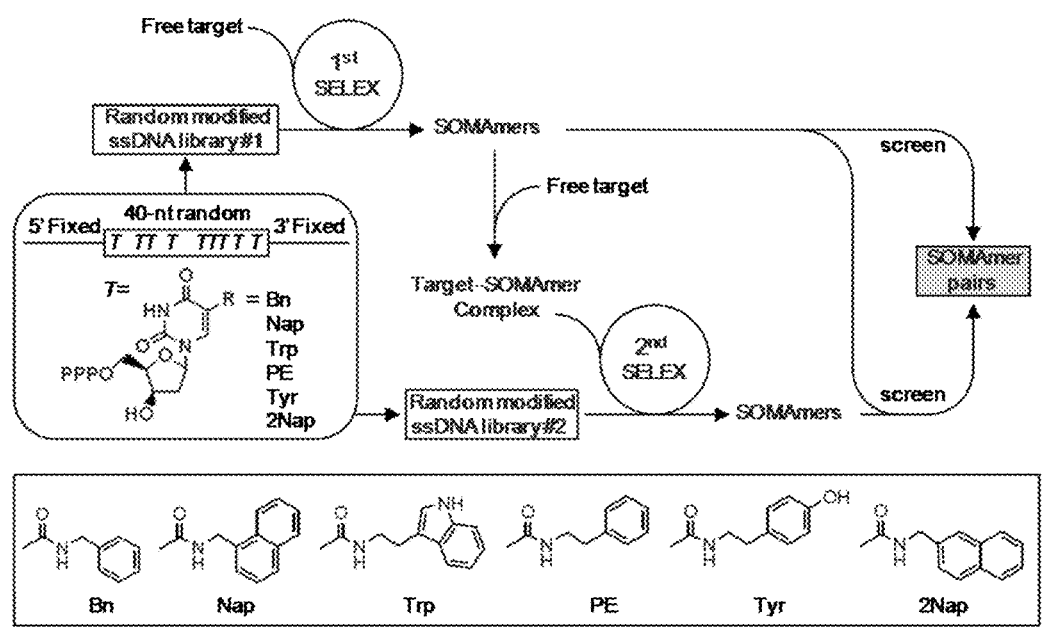
FIG. 1A depicts the general strategy for the isolation and validation of a SOMAmer (modified DNA aptamer) pair for a protein target.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Aptamer: The term aptamer, as used herein, refers to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule.

Analog: The term analog, as used herein, refers to a structural chemical analog as well as a functional chemical analog. A structural chemical analog is a compound having a similar structure to another chemical compound but differing by one or more atoms or functional groups. This difference may be a result of the addition of atoms or functional groups, absence of atoms or functional groups, the replacement of atoms or functional groups or a combination thereof. A functional chemical analog is a compound that has similar chemical, biochemical and/or pharmacological properties. The term analog may also encompass S and R stereoisomers of a compound.

Bioactivity: The term bioactivity, as used herein, refers to one or more intercellular, intracellular or extracellular process (e.g., cell-cell binding, ligand-receptor binding, cell signaling, etc.) which can impact physiological or pathophysiological processes.

C-5 Modified Pyrimidine: C-5 modified pyrimidine, as used herein, refers to a pyrimidine with a modification at the C-5 position. Examples of a C-5 modified pyrimidine include those described in U.S. Pat. Nos. 5,719,273, 5,945, 527, 7,947,447, as well as, U.S. Publication No. 2014/0058076, filed Feb. 27, 2014. Additional examples are provided herein.

Competitor Molecule: Competitor molecule or competitor, are used interchangeably to refer to any molecule that can form a non-specific complex with a non-target molecule. A "competitor molecule" or "competitor" is a population of different types of molecules or a particular or species of molecule. "Competitor molecules" or "competitors" refer to more than one such type of molecules. Competitor molecules include oligonucleotides, polyanions (e.g., heparin, single-stranded salmon sperm DNA, and polydextrans (e.g., dextran sulphate)), abasic phosphodiester polymers, dNTPs, and pyrophosphate. In the case of a kinetic challenge that uses a competitor, the competitor can also be any molecule that can form a non-specific complex with an aptamer. Such competitor molecules include polycations (e.g., spermine, spermidine, polylysine, and polyarginine) and amino acids (e.g., arginine and lysine).

Consensus Sequence: Consensus sequence, as used herein, refers to a nucleotide sequence that represents the most frequently observed nucleotide found at each position of a series of nucleic acid sequences subject to a sequence alignment.

Covalent Bond: Covalent bond or interaction refers to a chemical bond that involves the sharing of at least a pair of electrons between atoms.

Incubating: The term incubating (or incubation), as used herein, refers to controlled conditions in which components are placed together to promote a desired outcome. For example, a target (e.g., protein) and an aptamer may be incubated by putting them together to promote the binding of the aptamer with the target to form a complex. Further examples include putting the complex together with a second aptamer to incubate the complex and second aptamer for form a second complex (i.e., aptamer-protein-second aptamer). The controlled conditions for incubating include temperature, time, pH, salt concentration, and the type of mixture, of which non-limiting examples include a solution, an emulsion, a gel and a foam. Temperatures may range from about 21° C. to about 45° C. (or about 21, 22, 23, 24, 25, 26, 27, 28, 29, 30, 31, 32, 33, 34, 35, 36, 37, 38, 39, 40, 41, 42, 43, 44 or 45 degrees celcius). Preferably, the temperature is from about 28° C. to about 37° C. (or 28, 29, 30, 31, 32, 33, 34, 35, 36 or 37 degrees celcius), or about 28° C. or about 37° C. The time of incubation may include from about 1 minute to about 240 minutes (or 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235 or 240 minutes). Preferably, the incubation time is about 15 minutes, 30 minutes, 60 minutes, 120 minutes, 180 minutes or about 210 minutes. The pH conditions for incubation may range from about 5 to about 12 (or 5, 5.5, 6, 6.5, 7, 7.5, 8, 8.5, 9, 9.5, 10, 10.5, 11, 11.5 or 12). Preferably, the pH is about 6, 6.1, 6.2, 6.3, 6.4, 6.5, 6.6, 6.7, 6.8, 6.9, 7, 9. 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4 or 11.5). The above set of specific conditions are representative and non-limiting. Further, the same specific conditions for incubation may be used throughout the methods disclosed herein or may change at different steps of the methods disclosed herein.

Inhibit: The term inhibit, as used herein, means to prevent or reduce the expression of a peptide or a polypeptide to an extent that the peptide or polypeptide no longer has measurable activity or bioactivity; or to reduce the stability and/or reduce or prevent the activity of a peptide or a polypeptide to an extent that the peptide or polypeptide no longer has measurable activity or bioactivity.

Kinetic Challenge: Kinetic challenge, as used herein, refers to a process of enrichment for an aptamer affinity complex from a set of complexes that includes an aptamer affinity complex and non-specific complexes, by applying kinetic pressure and making use of the different affinity characteristics of the constituents of such classes of complexes, including dissociation rates. A kinetic challenge generally results in an increase in specificity, since aptamer-non-target complexes are typically reduced compared to aptamer-target complexes. As used herein, the term "kinetic pressure" refers to a means for providing an opportunity for the natural dissociation of complexes and/or inhibiting the rebinding of molecules that dissociate from a complex naturally. Kinetic pressure can be applied by the addition of a competitor molecule, or by sample dilution, or by extensive washes when complexes are bound to a solid support, or by any other means known to one skilled in the art. As one of ordinary skill in the art will appreciate, because a kinetic challenge generally depends upon the differing dissociation rates of aptamer affinity complexes and aptamer-non-target complexes, the duration of the kinetic challenge is chosen so as to retain a high proportion of aptamer affinity complexes while substantially reducing the number of aptamer-non-target complexes. For a kinetic challenge to be effective, the dissociation rate for the aptamer affinity complex is preferably significantly lower than those for aptamer-non-target complexes. Since an aptamer can be selected to include particular properties, the constituents of an aptamer affinity complex can be designed to have a comparatively low dissociation rate, i.e., slow off rate.

Modified: The term modified (or modify or modification) and any variations thereof, when used in reference to an oligonucleotide, means that at least one of the four constituent nucleotide bases (i.e., A, G, T/U, and C) of the oligonucleotide is an analog or ester of a naturally occurring nucleotide.

Modulate: The term modulate, as used herein, means to alter the expression level of a peptide, protein or polypeptide by increasing or decreasing its expression level relative to a reference expression level, and/or alter the stability and/or activity of a peptide, protein or polypeptide by increasing or decreasing its stability and/or activity level relative to a reference stability and/or activity level.

Non-covalent Bond: Non-covalent bond or non-covalent interaction refers to a chemical bond or interaction that does not involve the sharing of pairs of electrons between atoms. Examples of non-covalent bonds or interactions include hydrogen bonds, ionic bonds (electrostatic bonds), van der Waals forces and hydrophobic interactions.

Nucleic Acid: Nucleic acid, as used herein, refers to any nucleic acid sequence containing DNA, RNA and/or analogs thereof and may include single, double and multi-stranded forms. The terms "nucleic acid", "oligo", "oligonucleotide" and "polynucleotide" may be used interchangeably.

Pharmaceutically Acceptable: Pharmaceutically acceptable, as used herein, means approved by a regulatory agency of a federal or a state government or listed in the U.S. Pharmacopoeia or other generally recognized pharmacopoeia for use in animals and, more particularly, in humans.

Pharmaceutically Acceptable Salt: Pharmaceutically acceptable salt or salt of a compound (e.g., aptamer), as used herein, refers to a product that contains an ionic bond and is typically produced by reacting the compound with either an acid or a base, suitable for administering to an individual. A pharmaceutically acceptable salt can include, but is not limited to, acid addition salts including hydrochlorides, hydrobromides, phosphates, sulphates, hydrogen sulphates, alkylsulphonates, arylsulphonates, arylalkylsulfonates, acetates, benzoates, citrates, maleates, fumarates, succinates, lactates, and tartrates; alkali metal cations such as Li, Na, K, alkali earth metal salts such as Mg or Ca, or organic amine salts.

Pharmaceutical Composition: Pharmaceutical composition, as used herein, refers to formulation comprising an aptamer in a form suitable for administration to an individual. A pharmaceutical composition is typically formulated to be compatible with its intended route of administration. Examples of routes of administration include, but are not limited to, oral and parenteral, e.g., intravenous, intradermal, subcutaneous, inhalation, topical, transdermal, transmucosal, and rectal administration.

SELEX: The term SELEX, as used herein, refers to generally to the selection for nucleic acids that interact with a target molecule in a desirable manner, for example binding with high affinity to a protein; and the amplification of those selected nucleic acids. SELEX may be used to identify aptamers with high affinity to a specific target molecule. The term SELEX and "SELEX process" may be used interchangeably.

Sequence Identity: Sequence identity, as used herein, in the context of two or more nucleic acid sequences is a function of the number of identical nucleotide positions shared by the sequences (i.e., % identity=number of identical positions/total number of positions×100), taking into account the number of gaps, and the length of each gap that needs to be introduced to optimize alignment of two or more sequences. The comparison of sequences and determination of percent identity between two or more sequences can be accomplished using a mathematical algorithm, such as BLAST and Gapped BLAST programs at their default parameters (e.g., Altschul et al., *J. Mol. Biol.* 215:403, 1990; see also BLASTN at www.ncbi.nlm.nih.gov/BLAST). For sequence comparisons, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987)). As used herein, when describing the percent identity of a nucleic acid, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence.

SOMAmer: The term SOMAmer, as used herein, refers to an aptamer having improved off-rate characteristics. SOMAmers are alternatively referred to as Slow Off-Rate Modified Aptamers, and may be selected via the improved SELEX methods described in U.S. Pat. No. 7,947,447, entitled "Method for Generating Aptamers with Improved Off-Rates", which is incorporated by reference in its entirety. The terms aptamer and SOMAmer may be used interchangeably.

Spacer Sequence: Spacer sequence, as used herein, refers to any sequence comprised of small molecule(s) covalently bound to the 5'-end, 3'-end or both 5' and 3' ends of the nucleic acid sequence of an aptamer. Exemplary spacer sequences include, but are not limited to, polyethylene glycols, hydrocarbon chains, and other polymers or copolymers that provide a molecular covalent scaffold connecting the consensus regions while preserving aptamer binding activity. In certain aspects, the spacer sequence may be covalently attached to the aptamer through standard linkages such as the terminal 3' or 5' hydroxyl, 2' carbon, or base modification such as the C5-position of pyrimidines, or C8 position of purines.

Target Molecule: Target molecule (or target), as used herein, refers to any compound or molecule upon which a nucleic acid can act in a desirable manner (e.g., binding of the target, catalytically changing the target, reacting with the target in a way that modifies or alters the target or the functional activity of the target, covalently attaching to the target (as in a suicide inhibitor), and facilitating the reaction between the target and another molecule. Non-limiting examples of a target molecule include a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc. Virtually any chemical or biological effector may be a suitable target. Molecules of any size can serve as targets. A target can also be modified in certain ways to enhance the likelihood or strength of an interaction between the target and the nucleic acid. A target may also include any minor variation of a particular compound or molecule, such as, in the case of a protein, for example, variations in its amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules.

Ternary complex: Ternary complex, as used herein, refers to a complex of at least two aptamers and a target. In certain instances, the complex may comprise covalent, non-covalent or a combination of covalent and non-covalent interactions.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A or B, or including A and B. It is further to be understood that all base sizes or amino acid sizes, and all molecular weight or molecular mass values, given for nucleic acids or polypeptides are approximate, and are provided for description.

Further, ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise). Any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of mean±20% of the indicated range, value, or structure, unless otherwise indicated. As used herein, the terms "include" and "comprise" are open ended and are used synonymously. It should be understood that the terms "a" and "an" as used herein refer to "one or more" of the enumerated components. The use of the alternative (e.g., "or") should be understood to mean either one, both, or any combination thereof of the alternatives.

Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

II. Overview

In another aspect of this disclosure, the first aptamer and the second aptamer of the present disclosure may include up to about 100 nucleotides, up to about 95 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides.

In another aspect of this disclosure, the first C-5 pyrimidine modification scheme improves the off-rate or the rate of dissociation of the first aptamer compared to the first aptamer without the first C-5 pyrimidine modification scheme. In another aspect, the second C-5 pyrimidine modification scheme improves the off-rate or the rate of dissociation of the second aptamer compared to the second aptamer without the second C-5 pyrimidine modification scheme.

In another aspect of this disclosure, the first aptamer may be at least about 95% identical, at least about 90% identical, at least about 85% identical, at least about 80% identical, or at least about 75% identical to another nucleic acid sequence of another aptamer. In another aspect of this disclosure, the second aptamer may be at least about 95% identical, at least about 90% identical, at least about 85% identical, at least about 80% identical, or at least about 75% identical to another nucleic acid sequence of another aptamer.

In another aspect, the $K_d$ of the first or second aptamer to the target or target/aptamer complex is from about 1 nM to about 100 nM (or from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 90, 91, 92, 93, 94, 95, 96, 97, 98, 99 or 100 nM).

In another aspect, the $K_d$ is from about 4 nM to about 10 nM (or from 4, 5, 6, 7, 8, 9, or 10 nM).

In another aspect this disclosure, the first aptamer and/or second aptamer may have a dissociation constant ($K_d$) for the target or a target/aptamer complex of about 10 nM or less. In another exemplary embodiment, the first aptamer and/or second aptamer has a dissociation constant ($K_d$) for the target protein of about 15 nM or less. In yet another exemplary embodiment, the first aptamer and/or second aptamer has a dissociation constant ($K_d$) for the target protein of about 20 nM or less. In yet another exemplary embodiment, the first aptamer and/or second aptamer has a dissociation constant ($K_d$) for the target protein of about 25 nM or less. In yet another exemplary embodiment, the first aptamer and/or second aptamer has a dissociation constant ($K_d$) for the target protein of about 30 nM or less. In yet another exemplary embodiment, the first aptamer and/or second aptamer has a dissociation constant ($K_d$) for the target protein of about 35 nM or less. In yet another exemplary embodiment, the first aptamer and/or second aptamer has a dissociation constant ($K_d$) for the target protein of about 40 nM or less. In yet another exemplary embodiment, the first aptamer and/or second aptamer has a dissociation constant ($K_d$) for the target protein of about 45 nM or less. In yet another exemplary embodiment, the first aptamer and/or second aptamer has a dissociation constant ($K_d$) for the target protein of about 50 nM or less. In yet another exemplary embodiment, the first aptamer and/or second aptamer has a dissociation constant ($K_d$) for the target protein in a range of about 3-10 nM (or 3, 4, 5, 6, 7, 8, 9 or 10 nM). In yet another exemplary embodiment, the first aptamer and/or second aptamer has a dissociation constant ($K_d$) for the target protein in a range of about 0.02 nM to about 3 nM (or from 0.02, 0.03, 0.04, 0.05, 0.06, 0.07, 0.08, 0.09, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, 0.5, 0.52, 0.54, 0.56, 0.58, 0.6, 0.62, 0.64, 0.66, 0.68, 0.7, 0.72, 0.74, 0.76, 0.78, 0.8, 0.82, 0.84, 0.86, 0.88, 0.9, 0.92, 0.94, 0.96, 0.98, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 nM).

A suitable dissociation constant can be determined with a binding assay using a multi-point titration and fitting the equation $y=(max-min)(Protein)/(K_d+Protein)+min$ as described herein. It is to be understood that the determination of dissociation constants is highly dependent upon the conditions under which they are measured and thus these numbers may vary significantly with respect to factors such as equilibration time, etc.

In another aspect of this disclosure, the first aptamer and/or second aptamer comprise a rate of dissociation ($t_{1/2}$) from the target selected from the group consisting of a time ≥about 15 minutes, ≥about 30 minutes, ≥about 60 minutes, ≥about 90 minutes, ≥about 120 minutes, ≥about 150 minutes, ≥about 180 minutes, ≥about 210 minutes and ≥about 240 minutes.

The present disclosure further provides kits comprising a first aptamer and a second aptamer, wherein the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are different; and wherein the first aptamer has binding affinity for a target, and the second aptamer has binding affinity for the target and/or the first aptamer bound to the target.

In another aspect, the first aptamer has affinity for the target and not the second aptamer.

In another aspect, the second aptamer has binding affinity for the target and not the first aptamer.

In another aspect, the second aptamer has binding affinity for a complex formed by the association of the first aptamer with the target.

In another aspect, the first aptamer binding region of the target and the second aptamer binding region of the target are different regions. In a related aspect, the first aptamer and the second aptamer have non-competing binding sites on the target.

In another aspect, the first aptamer and the second aptamer, independently, comprise RNA, DNA or a combination thereof.

In another aspect, the first C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethyl-carboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the first C-5 pyrimidine modification scheme comprises a C-5 modified pyrimidine selected from the group consisting of a 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the first C-5 pyrimidine modification scheme comprises a C-5 modified pyrimidine selected from the group consisting of a 5-(N-benzylcarboxyamide)-2'-deoxyuridine (BndU), a 5-(N-tryptaminocarboxyamide)-2'-deoxyuridine (TrpdU) and a combination thereof. In another related aspect, the first C-5 pyrimidine modification scheme comprises a 5-(N-benzylcarboxyamide)-2'-deoxyuridine (BndU).

In another aspect, each uracil or thymine of the first aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine. In a related aspect, each uracil or thymine of the first aptamer is a 5-(N-benzylcarboxyamide)-2'-deoxyuridine (BndU).

In another aspect, the second C-5 pyrimidine modification scheme comprises a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine, a 5-(N-[1-(2,3-dihydroxypropyl)]carboxyamide)-2'-deoxyuridine and a combination thereof. In a related aspect, the second C-5 pyrimidine modification scheme comprises a C-5 modified pyrimidine selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof. In yet another related aspect, the second C-5 pyrimidine modification scheme comprises a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

In another aspect, each uracil or thymine of the second aptamer is a C-5 modified pyrimidine selected from the group consisting of 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-thiophenylmethylcarboxyamide)-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine and a 5-(N-[1-(2,3-dihydroxypropyl)]carboxyamide)-2'-deoxyuridine.

In a related aspect, each uracil or thymine of the second aptamer is a 5-(N-benzylcarboxyamide)-2'-deoxyuridine (BndU).

In another aspect, the first aptamer and the second aptamer, independently, are each from about 20 to 100 nucleotides in length (or from 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length). In a related aspect, the first aptamer and the second aptamer, independently, are from about 40 to about 100 nucleotides in length (or from 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides in length).

In another aspect, the first aptamer and/or the second aptamer further comprise a detectable moiety. In a related aspect, the detectable moiety is selected from the group consisting of a dye, a quantum dot, a radiolabel, an electrochemical functional group, an enzyme, an enzyme substrate, a ligand and a receptor.

In another aspect, the target comprises a protein or a peptide. In a related aspect, the target is a protein selected from the group consisting ANGPT2, TSP2, CRDL1, MATN2, GPVI, ESAM, C7, PLG, MMP-12, NPS-PLA2 and CdtA.

The present disclosure further provides that any of the methods disclosed herein may be subject to or comprise a kinetic challenge. In another aspect, the methods described herein further comprise the addition of a competitor molecule, a dilution step or one or more washes to improve the binding affinity of the aptamer with the target. In a related aspect, the competitor molecule is selected from the group consisting of an oligonucleotide, heparin, herring sperm DNA, salmon sperm DNA, dextran sulfate, polyanion, abasic phosphodiester polymer, dNTP, and pyrophosphate. In another aspect, the kinetic challenge comprises diluting the mixture containing any of the complexes as described herein, and incubating the mixture containing the aptamer affinity complex for a time selected from the group consisting of greater than or equal to 30 seconds, 1 minute, 2 minutes, 3 minutes, 4 minutes, 5 minutes, 10 minutes, 30 minutes, and 60 minutes. In another aspect, the kinetic challenge comprises diluting the mixture containing the aptamer affinity complex and incubating the mixture containing the aptamer affinity complex for a time such that the ratio of the measured level of aptamer affinity complex to the measured level of the non-specific complex is increased.

The present disclosure describes a composition comprising a first aptamer, second aptamer and a target, wherein the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are the same and wherein the first aptamer, second aptamer and the target are capable of forming a ternary complex.

The present disclosure further describes a method for detecting a target in a sample, the method comprising: contacting the sample with a first aptamer to form a mixture, wherein the first aptamer is capable of binding to the target to form a first complex; incubating the mixture under conditions that allow for the first complex to form; contacting the mixture with a second aptamer, wherein the second aptamer is capable of binding the first complex to form a second complex; incubating the mixture under conditions that allow for the second complex to form; detecting for the presence or absence of the first aptamer, the second aptamer, the target, the first complex or the second complex in the mixture, wherein the presence of the first aptamer, the second aptamer, the target, the first complex or the second complex indicates that the target is present in the sample; and wherein, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are the same.

In another aspect, the method for detecting a target in a sample comprises contacting the sample with the first and second aptamers simultaneously, incubating the mixture under conditions that allow the formation of a complex comprising the target and first and second aptamers, and detecting for the presence or absence of the first aptamer, the second aptamer, the target or the complex in the mixture, wherein the presence of the first aptamer, the second aptamer or the complex indicates that the target is present in the sample.

In another aspect, the first and second aptamers can both independently form a complex with the target. Specifically, the second aptamer can form a complex with the target alone as well as with the complex between the first aptamer and the target.

The present disclosure further describes a method comprising contacting a target with a first aptamer to form a mixture, wherein the first aptamer is capable of binding the target to form a first complex; incubating the mixture under conditions that allow for the first complex to form; contacting the mixture with a second aptamer, wherein the second aptamer is capable of binding the target to form a second complex; incubating the mixture under conditions that allow for the second complex to form; detecting for the presence or absence of the first aptamer and the second aptamer in the mixture, wherein the presence of both the first aptamer and second aptamer in the mixture indicates that the binding of the first aptamer to the target and the binding of the second aptamer to the target is non-competitive; and wherein, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are the same.

In another aspect, the first aptamer is capable of binding a protein selected from the group consisting ANGPT2, TSP2, CRDL1, MATN2, GPVI, ESAM, C7, PLG, MMP-12, NPS-PLA2 and CdtA.

In another aspect, the second aptamer is capable of binding a protein selected from the group consisting ANGPT2, TSP2, CRDL1, MATN2, GPVI, ESAM, C7, PLG, MMP-12, NPS-PLA2 and CdtA.

In another aspect, the first aptamer, the second aptamer and the target form a ternary complex, wherein the first aptamer binds the target in a first region of the target, and the second aptamer binds the target in a second region of the target, wherein the first region and second region of the target are overlapping or non-overlapping regions.

In another aspect, the composition comprises a first aptamer, a second aptamer and a target, wherein the first aptamer, second aptamer and the target are capable of forming a ternary complex, and wherein the first aptamer and second aptamer are, independently, from about 40 to about 50 nucleotides in length, and the first aptamer comprises a C-5 modified pyrimidine and the second aptamer comprises a C-5 modified pyrimidine, wherein the C-5 modified pyrimidine is selected from the group consisting of a 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-[N-(phenyl-3-propyl)carboxamide]-2'-deoxyuridine (PPdU), 5-[N-(2-thiophenemethyl)carboxamide]-2'-deoxyuridine (ThdU) (also referred to as 5-(N-thiophenylmethylcarboxyamide)-2'-deoxyuridine), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxamide)-2'-deoxyuridine chloride, 5-[N-(1-naphthylmethyl)carboxamide]-2'-deoxyuridine (NapdU), 5-[N-(2-naphthylmethyl)carboxyamide]-2'-deoxyuridine (2-NapdU), 5-[N-(1-naphthylethyl)carboxyamide]-2'-deoxyuridine (NEdU), 5-[N-(2-naphthylethyl)carboxyamide]-2'-deoxyuridine 2NEdU), 5-[N-(4-fluorobenzyl)carboxyamide]-2'-deoxyuridine FBndU), 5-[N-(4-hydroxyphenyl-2-ethyl)carboxamide]-2'-deoxyuridine (TyrdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine, 5-[N-(3-benzo[b]thiophene-2-ethyl)carboxamide]-2'-deoxyuridine (BTdU), 5-[N-(3-benzo[a]furan-2-ethyl)carboxamide]-2'-deoxyuridine (BFdU), 5-[N-(3,4-methylenedioxybenzyl)carboxamide]-2'-deoxyuridine (MBndU), 5-[N—((R)-2-tetrahydrofurylmethyl)carboxamide]-2'-deoxyuridine (RTHdU), 5-[N—((S)-2-tetrahydrofurylmethyl)carboxamide]-2'-deoxyuridine (STHFdU), 5-(N-2-imidazolylethylcarboxamide)-2'-deoxyuridine (ImiddU), 5-[N-(1-morpholino-2-ethyl)carboxamide]-2'-deoxyuridine (MOEdU), and wherein the C-5 modified pyrimidine of the first aptamer and the C-5 modified pyrimidine of the second aptamer are different C-5 modified pyrimidines.

In another aspect, the composition comprises a first aptamer, a second aptamer and a target, wherein the first aptamer, second aptamer and the target are capable of forming a ternary complex, and wherein the first aptamer and second aptamer are, independently, from about 40 to about 50 nucleotides in length, and the first aptamer comprises a C-5 modified pyrimidine and the second aptamer comprises a C-5 modified pyrimidine, wherein the C-5 modified pyrimidine is selected from the group consisting of a 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-[N-(phenyl-3-propyl)carboxamide]-2'-deoxyuridine (PPdU), 5-[N-(2-thiophenemethyl)carboxamide]-2'-deoxyuridine (ThdU), 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-[N-(1-naphthylmethyl)carboxamide]-2'-deoxyuridine (NapdU), 5-[N-(2-naphthylmethyl)carboxyamide]-2'-deoxyuridine (2-NapdU), 5-[N-(1-naphthylethyl)carboxyamide]-2'-deoxyuridine (NEdU), 5-[N-(2-naphthylethyl)carboxyamide]-2'-deoxyuridine 2NEdU), 5-[N-(4-fluorobenzyl)carboxyamide]-2'-deoxyuridine FBndU), 5-[N-(4-hydroxyphenyl-2-ethyl)carboxamide]-2'-deoxyuridine (TyrdU), 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine, 5-[N-(3-benzo[b]thiophene-2-ethyl)carboxamide]-2'-deoxyuridine (BTdU), 5-[N-(3-benzo[a]furan-2-ethyl)carboxamide]-2'-deoxyuridine (BFdU), 5-[N-(3,4-methylenedioxybenzyl)carboxamide]-2'-deoxyuridine (MBndU), 5-[N—((R)-2-tetrahydrofurylmethyl)carboxamide]-2'-deoxyuridine (RTHdU), 5-[N—((S)-2-tetrahydrofurylmethyl)carboxamide]-2'-deoxyuridine (STHFdU), 5-(N-2-imidazolylethylcarboxamide)-2'-deoxyuridine (ImiddU), 5-[N-(1-morpholino-2-ethyl)carboxamide]-2'-deoxyuridine (MOEdU), and wherein the C-5 modified pyrimidine of the first aptamer and the C-5 modified pyrimidine of the second aptamer are the same C-5 modified pyrimidines.

In another aspect, the mixture of the first aptamer and target are incubated under conditions that allow for the first complex to form. These conditions include a target (e.g., protein) to first aptamer ratio of about 10:1. Alternative ratios of target to first aptamer include from about 9:1, 8:1, 7:1, 6:1, 5:1, 4:1, 3:1, 2:1, 1:1, 1:2, 1:3, 1:4, 1:5, 1:6, 1:7, 1:8, 1:9 and 1:10. The conditions further include a temperature of about 37° C. Alternative temperatures include room temperature (or about 21° C.) or from about 21° C. to about 37° C. (or 21, 22, 23, 24, 25, 26, 27, 28, 29, 30, 31, 32, 33, 34, 35, 36 or 37° C.). The conditions also include times of incubation at the aforementioned ratio and temperature conditions, including from about 30 seconds to about 72 hours (or from about 30 seconds, 1 minute, 2, minutes, 5 minutes, 10, minutes, 15, minutes, 20 minutes, 30 minutes, 45 minutes, 1 hour, 2 hours, 3, hours, 4 hours, 5 hours, 6 hours, 7 hours, 8 hours, 9 hours, 10 hours, 12 hours, 15 hours, 20 hours, 24 hours, 30 hours, 36 hours, 40 hours, 44 hours, 48 hours, 50 hours, 55 hours, 60 hours, 65 hours, 70 hours or 72 hours).

In another aspect, the mixture of the second aptamer and target or the second aptamer and the first complex are incubated under conditions that allow for the second complex to form. These conditions include a target (e.g., protein) or first complex to second aptamer ratio of about 10:1. Alternative ratios of target or first complex to second aptamer include from about 9:1, 8:1, 7:1, 6:1, 5:1, 4:1, 3:1, 2:1, 1:1, 1:2, 1:3, 1:4, 1:5, 1:6, 1:7, 1:8, 1:9 and 1:10. The conditions further include a temperature of about 37° C. Alternative temperatures include room temperature (or about 21° C.) or from about 21° C. to about 37° C. (or 21, 22, 23, 24, 25, 26, 27, 28, 29, 30, 31, 32, 33, 34, 35, 36 or 37° C.). The conditions also include times of incubation at the aforementioned ratio and temperature conditions, including from about 30 seconds to about 72 hours (or from about 30 seconds, 1 minute, 2, minutes, 5 minutes, 10, minutes, 15, minutes, 20 minutes, 30 minutes, 45 minutes, 1 hour, 2 hours, 3, hours, 4 hours, 5 hours, 6 hours, 7 hours, 8 hours, 9 hours, 10 hours, 12 hours, 15 hours, 20 hours, 24 hours, 30 hours, 36 hours, 40 hours, 44 hours, 48 hours, 50 hours, 55 hours, 60 hours, 65 hours, 70 hours or 72 hours).

In another aspect, the binding affinity (or $K_d$) is determined by the methods selected from a radiolabel filter-binding assay and a fluorescence bead-based Luminex assay.

The present disclosure further describes a method comprising contacting a first aptamer with a solid support, wherein the first aptamer comprises a linker and a tag, wherein the tag is capable of binding to the solid support; contacting a target with the first aptamer, wherein the first aptamer has binding affinity for the target, and the first aptamer binds the target to form a first complex; contacting the first complex with a plurality of aptamers, wherein at least one aptamer of the plurality of aptamers binds the first complex to form a second complex; partitioning the second complex from the remaining plurality of aptamers; dissociating the second complex; amplifying the at least one aptamer; and identifying the at least one aptamer that is capable of binding the first complex.

The present disclosure further describes a method comprising contacting a first aptamer with a solid support, wherein the first aptamer comprises a linker and a tag, wherein the tag is capable of binding to the solid support; contacting a target with the first aptamer, wherein the first aptamer has binding affinity for the target, and the first aptamer binds the target to form a first complex; contacting the first complex with a plurality of aptamers, wherein one or more aptamers of the plurality of aptamers bind the first complex to form a second complex; partitioning the second complex from the remaining plurality of aptamers; dissociating the second complex; amplifying the one or more aptamers and identifying the one or more aptamers that are capable of binding the first complex.

The present disclosure further describes a method comprising contacting a first aptamer with a solid support, wherein the first aptamer comprises a linker and a tag, wherein the tag is capable of binding to the solid support; contacting a target with the first aptamer, wherein the first aptamer has binding affinity for the target, and the first aptamer binds the target to form a first complex; contacting the first complex with a plurality of aptamers to form a second complex, wherein the second complex comprises the first aptamer, the target and a second aptamer; partitioning the second complex from the remaining plurality of aptamers; dissociating the second complex; amplifying the second aptamer and identifying the second aptamer that is capable of binding the first complex.

In another aspect, the first aptamer comprises a C-5 modified pyrimidine.

In another aspect, the at least one aptamer comprises a C-5 modified pyrimidine.

In another aspect, at least 10%, 20%, 30%, 40%, 50%, 60%, 70%, 80%, 90% or 100% of the aptamers of the plurality of aptamers comprise a C-5 modified pyrimidine.

In another aspect, the tag binds the solid support.

In another aspect, the remaining plurality of aptamers have less binding affinity for the first complex than the at least one aptamer.

In another aspect, the tag is at the 5'-end or the 3'-end of the first aptamer.

In another aspect, the linker is a photo-cleavable linker.

In another aspect, the target is s selected from the group consisting of a protein, a peptide, a carbohydrate, a glycoprotein, a cell and a tissue.

In another aspect, the first aptamer comprises a first C-5 pyrimidine modification scheme, the at least one aptamer comprises a second C-5 pyrimidine modification scheme, and wherein the first C-5 pyrimidine modification scheme and the second C-5 pyrimidine modification scheme are the same or are different.

In another aspect, the first aptamer comprises a first C-5 pyrimidine modification scheme, the one or more aptamers comprise a second C-5 pyrimidine modification scheme, and wherein the first C-5 pyrimidine modification scheme and the second C-5 pyrimidine modification scheme are the same or are different.

In another aspect, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are the same or are different.

In another aspect, the at least one aptamer has binding affinity for the target and not the first aptamer.

In another aspect, the at least one aptamer binds the target of the first complex and not the first aptamer of the first complex.

In another aspect, the at least one aptamer binds the target and the first aptamer of the first complex.

In another aspect, the one or more aptamers have binding affinity for the target and not the first aptamer.

In another aspect, the one or more aptamers bind the target of the first complex and not the first aptamer of the first complex.

In another aspect, the one or more aptamers bind the target and the first aptamer of the first complex.

In another aspect, the second aptamer has binding affinity for the target and not the first aptamer.

In another aspect, the second aptamer binds the target of the first complex and not the first aptamer of the first complex.

In another aspect, the second aptamer binds the target and the first aptamer of the first complex.

In another aspect, the solid support is selected from the group consisting of a microscope slide, a cyclo-olefin copolymer substrate, a membrane, a plastic substrate, a paramagnetic bead, charged paper, nylon, a Langmuir-Bodgett film, glass, a germanium substrate, a silicon substrate, a silicon wafer chip, a flow through chip, a microbead, a polytetrafluoroethylene substrate, a polystyrene substrate, a gallium arsenide substrate, a gold substrate and a silver substrate.

In another aspect, the solid support is a streptavidin bead.

In another aspect, the amplification step results in the formation of a candidate mixture of aptamers.

In another aspect, the method further comprises contacting the first complex with the candidate mixture of aptamers to further select for aptamers with binding affinity for the first complex.

The disclosure further provides for a method comprising: a) contacting a first aptamer with a solid support, wherein the first aptamer comprises a linker and a tag, wherein the tag is capable of binding to the solid support; b) contacting a target with the first aptamer, wherein the first aptamer has binding affinity for the target, and the first aptamer binds the target to form a first complex; c) contacting the first complex with a plurality of aptamers to form a plurality of second complexes, wherein each of the plurality of second complexes comprises the first aptamer, the target and a second aptamer, and wherein the plurality of second complexes comprises a plurality of second aptamers; d) partitioning the plurality of second complexes from the aptamers of the plurality of aptamers, wherein at least one aptamer of the plurality of aptamers has less binding affinity for the first complex than at least one of the second aptamers of the plurality of second complexes; e) dissociating the plurality of second complexes; f) amplifying the plurality of second aptamers to form a first candidate mixture of aptamers; g) at least one time, repeating steps a) through f) with the first candidate mixture of aptamers to form a second candidate mixture of aptamers, or at last two times, repeating steps a) through f) to form a third candidate mixture of aptamers, or at last three times, repeating steps a) through f) to form a fourth candidate mixture of aptamers, or at last four times, repeating steps a) through f) to form a fifth candidate mixture of aptamers, or at last five times, repeating steps a) through f) to form a sixth candidate mixture of aptamers, or at last six times, repeating steps a) through f) to form a seventh candidate mixture of aptamers, or at last seven times, repeating steps a) through f) to form an eighth candidate mixture of aptamers, or at last eight times, repeating steps a) through f) to form a ninth candidate mixture of aptamers, or at last nine times, repeating steps a) through f) to form a tenth candidate mixture of aptamers, or at last ten times, repeating steps a) through f) to form a eleventh candidate mixture of aptamers, or at last eleven times, repeating steps a) through f) to form a twelfth candidate mixture of aptamers, or at last twelve times, repeating steps a) through f) to form a thirteenth candidate mixture of aptamers, or at last thirteen times, repeating steps a) through f) to form a fourteenth candidate mixture of aptamers, or at last fourteen times, repeating steps a) through f) to form a fifteenth candidate mixture of aptamers, or at last fifteen times, repeating steps a) through f) to form a sixteenth candidate mixture of aptamers and h) identifying at least one of the aptamers of the plurality of second aptamers that is capable of binding the first complex.

The disclosure further provides for a method comprising a) contacting a first aptamer with a solid support, wherein the first aptamer comprises a linker and a tag, wherein the tag is capable of binding to the solid support; b) contacting a target with the first aptamer, wherein the first aptamer has binding affinity for the target, and the first aptamer binds the target to form a first complex; c) contacting the first complex with a plurality of aptamers to form a plurality of second complexes, wherein each of the plurality of second complexes comprises the first aptamer, the target and a second aptamer, and wherein the plurality of second complexes comprises a plurality of second aptamers; d) partitioning the plurality of second complexes from the aptamers of the plurality of aptamers, wherein at least one aptamer of the plurality of aptamers has less binding affinity for the first complex than at least one of the second aptamers of the plurality of second complexes; e) dissociating the plurality of second complexes; f) quantifying the plurality of second aptamers to obtain a quantitative value; g) repeating steps a) through f) until the ratio of the quantitative value to a reference value remains unchanged or decreases relative to the ratio of the quantitative value to the reference value of the previous repeating of steps a) through f), wherein the reference value is based on quantifying a plurality of control aptamers exposed to the method of steps a) through f) without the target; h) identifying at least one of the aptamers of the plurality of second aptamers that is capable of binding the first complex.

In another aspect, the tag is biotin.

A. SELEX

SELEX generally includes preparing a candidate mixture of nucleic acids, binding of the candidate mixture to the desired target molecule to form an affinity complex, separating the affinity complexes from the unbound candidate nucleic acids, separating and isolating the nucleic acid from the affinity complex, purifying the nucleic acid, and identifying a specific aptamer sequence. The process may include multiple rounds to further refine the affinity of the selected aptamer. The process can include amplification steps at one or more points in the process. See, e.g., U.S. Pat. No. 5,475,096, entitled "Nucleic Acid Ligands". The SELEX process can be used to generate an aptamer that covalently binds its target as well as an aptamer that non-covalently binds its target. See, e.g., U.S. Pat. No. 5,705,337 entitled "Systematic Evolution of Nucleic Acid Ligands by Exponential Enrichment: Chemi-SELEX."

The SELEX process can be used to identify high-affinity aptamers containing modified nucleotides that confer improved characteristics on the aptamer, such as, for example, improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides", which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-NH$_2$), 2'-fluoro (2'-F), and/or 2'-O-methyl (2'-OMe). See also, U.S. Pat. No. 8,409,795, entitled "SELEX and PHOTOSELEX", which describes nucleic acid libraries having expanded physical and chemical properties and their use in SELEX and photoSELEX.

SELEX can also be used to identify aptamers that have desirable off-rate characteristics. See, for example, U.S. Pat. No. 7,947,447, entitled "Method for Generating Aptamers with Improved Off-Rates", which describes improved SELEX methods for generating aptamers that can bind to target molecules. As mentioned above, these slow off-rate aptamers are known as "SOMAmers." Methods for producing aptamers or SOMAmers and photoaptamers or SOMAmers having slower rates of dissociation from their respective target molecules are described. The methods involve contacting the candidate mixture with the target molecule, allowing the formation of nucleic acid-target complexes to occur, and performing a slow off-rate enrichment process wherein nucleic acid-target complexes with fast dissociation rates will dissociate and not reform, while complexes with slow dissociation rates will remain intact. Additionally, the methods include the use of modified nucleotides in the production of candidate nucleic acid mixtures to generate aptamers or SOMAmers with improved off-rate performance.

A variation of this assay employs aptamers that include photoreactive functional groups that enable the aptamers to covalently bind or "photocrosslink" their target molecules. See, e.g., U.S. Pat. No. 6,544,776 entitled "Nucleic Acid Ligand Diagnostic Biochip." These photoreactive aptamers are also referred to as photoaptamers. See, e.g., U.S. Pat. No. 5,763,177, U.S. Pat. No. 6,001,577 and U.S. Pat. No. 6,291,184, each of which is entitled "Systematic Evolution of Nucleic Acid Ligands by Exponential Enrichment: Photoselection of Nucleic Acid Ligands and Solution SELEX," see also, e.g., U.S. Pat. No. 6,458,539, entitled "Photoselection of Nucleic Acid Ligands." After the microarray is contacted with the sample and the photoaptamers have had an opportunity to bind to their target molecules, the photoaptamers are photoactivated, and the solid support is washed to remove any non-specifically bound molecules. Harsh wash conditions may be used, since target molecules that are bound to the photoaptamers are generally not removed, due to the covalent bonds created by the photoactivated functional group(s) on the photoaptamers.

In both of these assay formats, the aptamers or SOMAmers are immobilized on the solid support prior to being contacted with the sample. Under certain circumstances, however, immobilization of the aptamers or SOMAmers prior to contact with the sample may not provide an optimal assay. For example, pre-immobilization of the aptamers or SOMAmers may result in inefficient mixing of the aptamers or SOMAmers with the target molecules on the surface of the solid support, perhaps leading to lengthy reaction times and, therefore, extended incubation periods to permit efficient binding of the aptamers or SOMAmers to their target molecules. Further, when photoaptamers or photoSOMAmers are employed in the assay and depending upon the material utilized as a solid support, the solid support may tend to scatter or absorb the light used to effect the formation of covalent bonds between the photoaptamers or photoSOMAmers and their target molecules. Moreover, depending upon the method employed, detection of target molecules bound to their aptamers or photoSOMAmers can be subject to imprecision, since the surface of the solid support may also be exposed to and affected by any labeling agents that are used. Finally, immobilization of the aptamers or SOMAmers on the solid support generally involves an aptamer or SOMAmer-preparation step (i.e., the immobilization) prior to exposure of the aptamers or SOMAmers to the sample, and this preparation step may affect the activity or functionality of the aptamers or SOMAmers.

SOMAmer assays that permit a SOMAmer to capture its target in solution and then employ separation steps that are designed to remove specific components of the SOMAmer-target mixture prior to detection have also been described (see U.S. Pat. No. 7,855,054, entitled "Multiplexed Analyses of Test Samples"). The described SOMAmer assay methods enable the detection and quantification of a non-nucleic acid target (e.g., a protein target) in a test sample by detecting and quantifying a nucleic acid (i.e., a SOMAmer). The described methods create a nucleic acid surrogate (i.e., the SOMAmer) for detecting and quantifying a non-nucleic acid target, thus allowing the wide variety of nucleic acid technologies, including amplification, to be applied to a broader range of desired targets, including protein targets.

Embodiments of the SELEX process in which the target is a peptide are described in U.S. Pat. No. 6,376,190, entitled "Modified SELEX Processes Without Purified Protein."

B. Slow Off-Rate Aptamers (SOMAmers)

Slow off-rate aptamers (SOMAmer reagents) have transformed the fields of proteomics, biomarker discovery, and medical diagnostics. It is now possible to measure >1000 proteins simultaneously and with high accuracy in a small sample (0.1 mL) of serum, plasma, CSF, or tissue lysate. The application of this highly multiplexed assay (SOMAscan) has led to the discovery of biomarkers in infectious, pulmonary, oncological, cardiovascular, renal and neurological diseases. SOMAmers have expanded range of protein targets and improved binding properties compared to conventional aptamers, because they contain deoxyuridine residues that are modified at their 5-position with hydrophobic aromatic functional groups that mimic amino acid side-chains. SOMAmers are generated in vitro by the SELEX process (Systematic Evolution of Ligands by Exponential Enrichment) which consists of multiple rounds of selection with kinetic challenge, partitioning, and amplification.

C. Chemical Modifications to Aptamers

Aptamers may contain modified nucleotides that improve is properties and characteristics. Non-limiting examples of such improvements include, in vivo stability, stability against degradation, binding affinity for its target, and/or improved delivery characteristics.

Examples of such modifications include chemical substitutions at the ribose and/or phosphate and/or base positions of a nucleotide. SELEX process-identified aptamers containing modified nucleotides are described in U.S. Pat. No. 5,660,985, entitled "High Affinity Nucleic Acid Ligands Containing Modified Nucleotides," which describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe). See also, U.S. Pat. No. 8,409,795, entitled "SELEX and PHOTOSELEX," which describes nucleic acid libraries having expanded physical and chemical properties and their use in SELEX and photoSELEX.

Specific examples of a C-5 modification include substitution of deoxyuridine at the C-5 position with a substituent independently selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

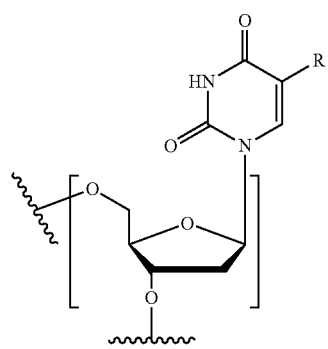

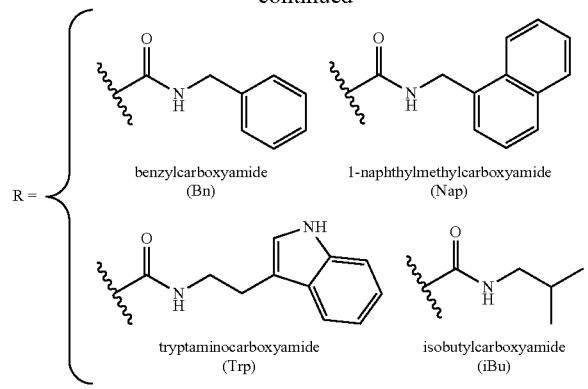

Chemical modifications of a C-5 modified pyrimidine can also be combined with, singly or in any combination, 2'-position sugar modifications, modifications at exocyclic amines, and substitution of 4-thiouridine and the like.

Representative C-5 modified pyrimidines include: 5-(N-benzylcarboxyamide)-2'-deoxyuridine (BndU), 5-(N-benzylcarboxyamide)-2'-O-methyluridine, 5-(N-benzylcarboxyamide)-2'-fluorouridine, 5-(N-isobutylcarboxyamide)-2'-deoxyuridine (iBudU), 5-(N-isobutylcarboxyamide)-2'-O-methyluridine, 5-(N-isobutylcarboxyamide)-2'-fluorouridine, 5-(N-tryptaminocarboxyamide)-2'-deoxyuridine (TrpdU), 5-(N-tryptaminocarboxyamide)-2'-O-methyluridine, 5-(N-tryptaminocarboxyamide)-2'-fluorouridine, 5-(N-[1-(3-trimethylamonium)propyl]carboxyamide)-2'-deoxyuridine chloride, 5-[N-(1-naphthylmethyl)carboxyamide]-2'-deoxyuridine (NapdU), 5-[N-(2-naphthylmethyl)carboxyamide]-2'-deoxyuridine (2-NapdU), 5-(N-naphthylmethylcarboxyamide)-2'-O-methyluridine, 5-(N-naphthylmethylcarboxyamide)-2'-fluorouridine or 5-(N-[1-(2,3-dihydroxypropyl)]carboxyamide)-2'-deoxyuridine.

If present, a modification to the nucleotide structure can be imparted before or after assembly of the polynucleotide. A sequence of nucleotides can be interrupted by non-nucleotide components. A polynucleotide can be further modified after polymerization, such as by conjugation with a labeling component.

Additional non-limiting examples of modified nucleotides (e.g., C-5 modified pyrimidine) that may be incorporated into the nucleic acid sequences of the present disclosure include the following:

U

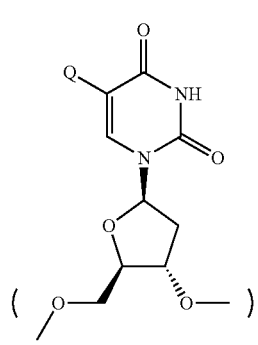

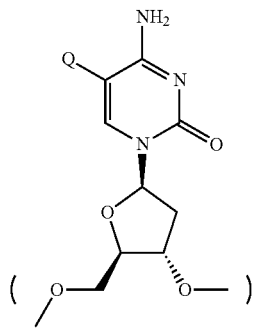
C
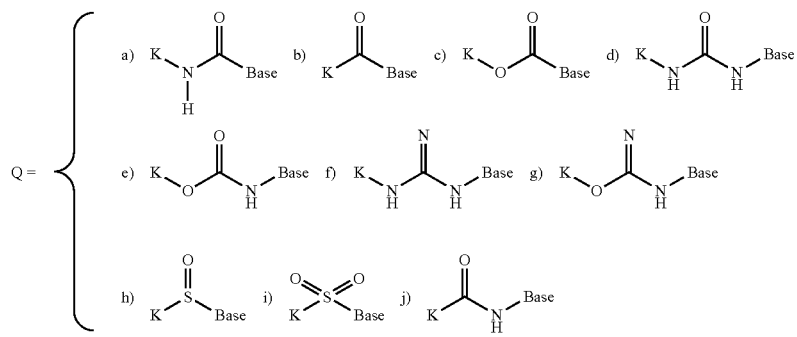
Base = Uridine (U) or Cytidine(C) (attachment is to the 5-position)
K = R' group plus (CH$_2$)$_n$ connecting group, where n = 0-3
R' is defined as follows:
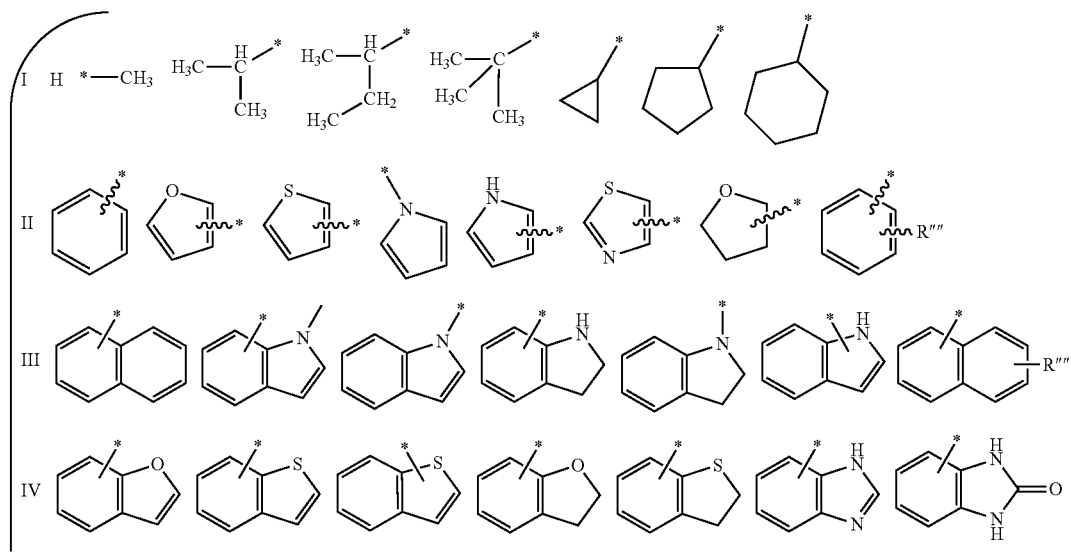

-continued

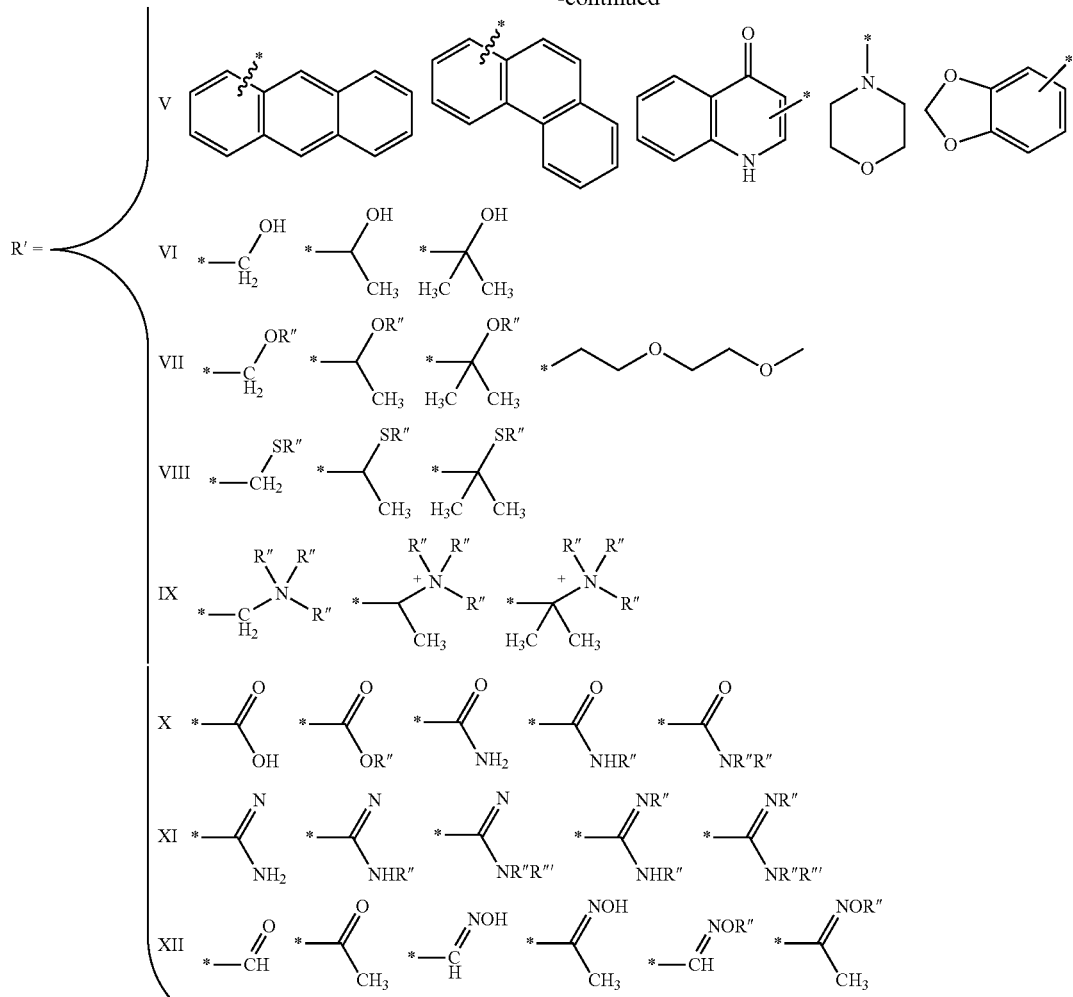

*Denotes point of attachement of the R' group to (CH₂)ₙ connecting group

And, R", R'" and R"" are defined as follows:
wherein

R"" is selected from the group consisting of a branched or linear lower alkyl (C1-C20); hydroxyl (OH), halogen (F, Cl, Br, I); nitrile (CN); boronic acid (BO₂H₂); carboxylic acid (COOH); carboxylic acid ester (COOR"); primary amide (CONH₂); secondary amide (CONHR"); tertiary amide (CONR"R'"); sulfonamide (SO₂NH₂); N-alkylsulfonamide (SONHR");

wherein

R", R'" are independently selected from a group consisting of a branched or linear lower alkyl (C1-C2)); phenyl (C₆H₅); an R"" substituted phenyl ring (R""C₆H₄); wherein R"" is defined above; a carboxylic acid (COOH); a carboxylic acid ester (COOR""); wherein R"" is a branched or linear lower alkyl (C1-C20); and cycloalkyl; wherein R"=R'"=(CH₂)n; wherein n=2-10.

Further, C-5 modified pyrimidine nucleotides include the following:

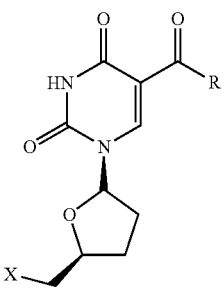

X = triphosphate wherein R is selected from one of the following moieties:
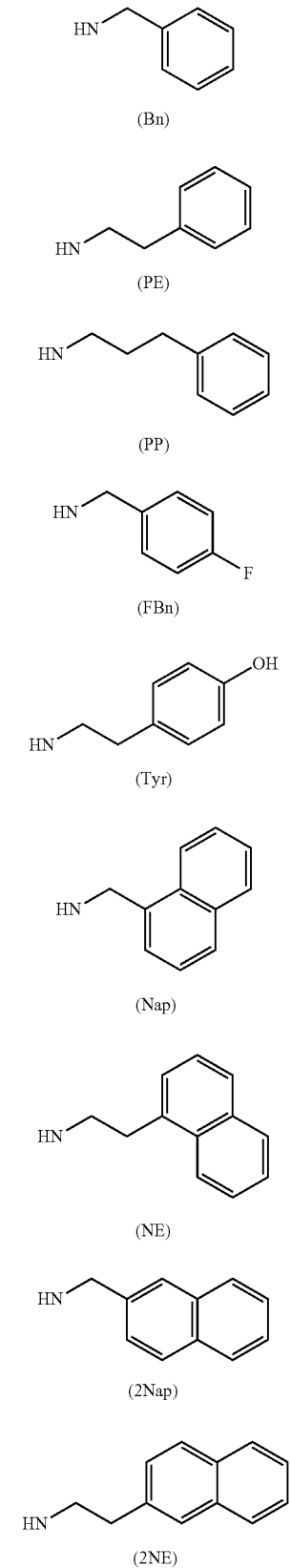
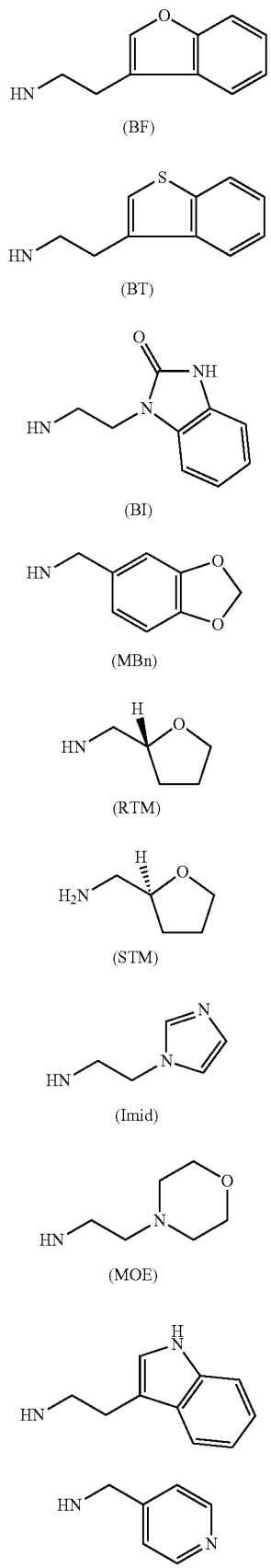

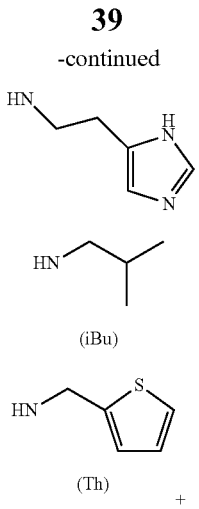

For nomenclature purposes and by way of example, where the R group is defined as 6a (or Bn) above, the nucleotide is named 5-(N-benzylcarboxyamide)-2'-deoxyuridine (BndU); where the R group is defined as 6f (or Nap) above, the nucleotide is named 5-[N-(1-naphthylmethyl)carboxyamide]-2'-deoxyuridine (NapdU) and where the R group is defined as 6 h (or 2Nap) above, the nucleotide is names 5-[N-(2-naphthylmethyl)carboxyamide]-2'-deoxyuridine (2-NapdU).

In some embodiments, the modified nucleotide confers nuclease resistance to the oligonucleotide. In some embodiments, the modified nucleotide is selected from the group consisting of chemical formulas 6a to 6v. A pyrimidine with a substitution at the C-5 position is an example of a modified nucleotide. Modifications can include backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present on the sugar of a nucleotide may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, polyethylene glycol (PEG) polymers in one embodiment ranging from about 10 to about 80 kDa, PEG polymers in another embodiment ranging from about 20 to about 60 kDa, or other hydrophilic or hydrophobic biological or synthetic polymers. In one embodiment, modifications are of the C-5 position of pyrimidines. These modifications can be produced through an amide linkage directly at the C-5 position or by other types of linkages.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

D. Kits Comprising Compositions

The present disclosure provides kits comprising a first aptamer and/or second aptamer described herein. Such kits can comprise, for example, (1) a first aptamer (e.g., a target capture aptamer) and/or a second aptamer (e.g., a target detection aptamer); and (2) at least one pharmaceutically acceptable carrier, such as a solvent or solution. Additional kit components can optionally include, for example: (1) any of the pharmaceutically acceptable excipients identified herein, such as stabilizers, buffers, etc., (2) at least one container, vial or similar apparatus for holding and/or mixing the kit components; and (3) delivery apparatus.

The following examples are provided to illustrate certain particular features and/or embodiments. These examples should not be construed to limit the disclosure to the particular features or embodiments described.

EXAMPLES

Example 1: Materials and Methods

This example provides a summary of the general materials and methods used to select and identify DNA aptamer pairs for target detection (e.g., protein target).

Proteins Used for SELEX.

*C. difficile* binary toxin (CdtA) was produced in recombinant, His$_{10}$-tagged form as described. Human proteins available in recombinant, tagged form (R&D Systems, Minneapolis, Minn., USA) included angiopoietin-2 (Cat. No. 623-AN/CF), TSP2 (Cat. No. 1635-T2), CRDL1 (Cat. No. 1808-NR), MATN2 (Cat. No. 3044-MN/CF), GPVI (Cat. No. 3627-GP), which were His-tagged, and ESAM (Cat. No. 2688-EC) as an Fc-fusion. Native human proteins purified from plasma included C7 (Quidel, San Diego, Calif., USA, Cat. No. A405) and plasminogen (Athens Research & Technology, Athens, Ga., USA, Cat. No. 16-16-161200); both were biotinylated using EZ-Link NHS-PEG4-Biotin (Thermo, Rockford, Ill., USA, Cat. No 21329) as described.

Aptamer Synthesis.

Truncated synthetic aptamers that contained the 40-nucleotide target-binding region and five nucleotides on each end were prepared via standard phosphoramidite chemistry using modified nucleotides. AB-H 50mers contained a 5'-biotin-dA hexaethyleneglycol spacer for easy coupling to streptavidin (SA), and a 3' inverted dT nucleotide (idT) for improved exonuclease stability.

Menu Aptamers (SOMAmers) and Sandwich SELEX.

Menu aptamers as primary binding agents to all protein targets had been isolated via SELEX and AB-H 50-mers were prepared as described above. As an alternative to AB-H aptamers, PBDC (photocleavable linker with biotin and a flurophore) aptamers were used in a modified SELEX process. The aptamers were "heat-cooled" to ensure their proper renaturation by heating to 95° C. for 3 minutes in SB18T and slowly cooling to 37° C. Activity was confirmed in equilibrium binding and in pull-down assays. For sandwich SELEX, the published selection protocol was modified as follows. The proteins were complexed with the AB-H versions of the cognate menu aptamers immediately prior to each round of SELEX. For R1, 100 µl of 500 nM protein (50 pmol) were mixed with 5 µl of 5 µM (25 pmol) heat-cooled aptamers and incubated for 30 min at 37° C. to allow complex formation. For subsequent rounds, 10 µl of 500 nM protein (5 pmol) and 2 µl of 5 µM (10 pmol) aptamers (2-fold excess) were used. Specific counter-selection beads to reduce background due to non-specific aptamer-aptamer interactions were prepared fresh in each round of SELEX. In brief, 2 µl of 5 µM (10 pmol) heat-cooled AB-H aptamers were added to 40 µl of 2.5 mg/ml SA beads in SB18T and shaken for 15 minutes to allow immobilization. The beads were then washed to remove residual free aptamers, resuspended in 50 µl SB18T and added to the counter-selection plate along with 10 µl Hexa-His (AnaSpec, Fremont, Calif., USA, Cat. No 24420) coated beads, or with 50 µl SA beads or Protein G beads according to the downstream partitioning method. Buffer SB18T (40 mM HEPES pH 7.5, 0.1 M NaCl, 5 mM KCl, 5 mM $MgCl_2$, 0.05% Tween-20) was used for SELEX and for all subsequent binding assays. The starting library consisted of 1 nmol ($10^{14}$-$10^{15}$) sequences of modified DNA sequences containing 40 consecutive randomized positions flanked by fixed sequences for PCR amplification. Separate libraries with different modified nucleotides were used, including 5-(N-tryptaminocarboxyamide)-2'-deoxyuridine (TrpdU), 5-(N-[2-naphthylmethyl]carboxyamide)-2'-deoxyuridine (2NapdU), and 5-(N-phenethylcarboxyamide)-2'-deoxyuridine (PEdU). A kinetic challenge with 5 mM dextran sulfate was performed from SELEX round 2 forward to favor slow off-rates. Partitioning of the target-aptamer complexes was achieved with paramagnetic Dynabeads® (Life Technologies, Carlsbad, Calif., USA), using His-tag 2 (Cat. No. 101-04D) for His-tagged proteins, Protein G (Cat. No. 100-04D) for Fc-fusion proteins, and MyOne Streptavidin C1 (Cat. No. 350-02D) beads for biotinylated targets, respectively. Selected DNA was eluted from the beads with sodium perchlorate elution buffer (1.8 M $NaClO_4$, 40 mM PIPES, 1 mM EDTA, 0.05% Triton X-100, pH 6.8) for 5 min, then captured on primer beads and processed for PCR and primer extension to obtain the sense-strands with the modified nucleotides using KOD XL DNA polymerase.

For the modified sandwich SELEX, partitioning of the target-aptamer complex was accomplished with streptavidin (SA) beads that bind the biotin-tag on the primary PBDC aptamer. This is in contrast to the AB-H aptamer based SELEX, where the biotin-tag is on the target. This modified method allowed for the use of untagged targets in sandwich SELEX. The selected DNA aptamers from the library were harvested via photocleavage (2 times at 7 minutes with shaking under a blacklight) of tripartite complexes from the SA beads instead of elution with sodium perchlorate, and processed for PCR and eDNA preparation.

DNA Sequencing and Comparative Sequence Analysis.

Aptamer pools obtained in SELEX were cloned using the PCR-Script Amp Cloning Kit (Agilent, Santa Clara, Calif., USA, Cat. No. 211189) and sequences of individual clones were determined on an ABI Prism 3730 (SeqWright, Houston, Tex.). Aptamers obtained in SELEX with complexed vs free protein were compared to identify common patterns, using customized, flexible alignment algorithms with pattern identity threshold=0.5-0.9, family cluster cutoff=0.5-0.9, sequence match threshold=0.8, and equivalence mismatches=5.

Equilibrium Binding Assays and Competition Assays.

Full-length aptamers isolated in SELEX and their synthetic, truncated counterparts were first evaluated for binding to free protein and then to pre-formed protein-menu aptamer complexes (stoichiometric ratio 1:1) to determine and compare the equilibrium binding constants, $K_d$'s, in filter-binding assays. Efficient partitioning of the complexes onto nylon membranes was achieved with Zorbax PSM-300A (Agilent, Santa Clara, Calif., USA), except for complexes with GPVI, where Dynabeads® His-tag 2 (Life Technologies, Carlsbad, Calif., USA, Cat. No. 101-04D) were used instead. Sandwich aptamer candidates were further tested in competition binding assays, where radiolabeled aptamers (~0.01 nM) were incubated with target proteins over a range of concentrations (0.001 nM to 100 nM) in the presence of 100-fold excess (10 nM) unlabeled menu aptamer as competitors.

Sandwich Filter-Binding Assays.

Two variations of filter-binding sandwich assays were performed to obtain 12-pt binding curves. The first method involved equilibrium binding of protein and radiolabeled, full-length detection aptamer, followed by partitioning (30 min with intermittent shaking) with specific capture beads that were prepared by immobilizing AB-H menu aptamers on SA beads. The second method was based on the formation of tripartite complexes during equilibrium binding of protein, radiolabeled detection aptamer (full-length, non-biotinylated) and excess (10 nM) unlabeled, AB-H menu aptamer, followed by partitioning (5 min with intermittent shaking) with SA beads. Both methods yielded comparable results. As controls, all sequences were tested in separate assays where the capture agent was omitted, to identify non-specific background due to SA bead binding. These clones, along with sequences resulting in non-titratable signals due to direct interaction of capture and detection aptamer, were removed from further analysis.

Multiplexed Sandwich Screening Assays.

The Luminex platform was used for the multiplexed, pair-wise screening of aptamers (AB-H 50mers) in sandwich binding format. Capture bead preparation and binding assays were performed in MSBVN12 filter plates (EMD Millipore Corp., Billerica, Mass., USA) pre-wet with buffer SB17T (SB18T supplemented with 1 mM EDTA). Different types of LumAvidin® Microspheres (Luminex Corporation, Austin, Tex., Cat. No. L100-L101-01 through L100-L116-01) were dispensed into separate wells (100,000 beads per well) and washed 3×1 min with 180 µl SB17T by vacuum filtration. Aptamers were heat-cooled, 80 µl of 50 nM stocks of each capture aptamer for a given protein target were added to a different bead type, and the plate was shaken (20 min at RT, 1100 rpm) to allow for immobilization. The beads were then washed for 5 min each with 100 µl 50 nM streptavidin and with 10 mM biotin in SB17T, then 4×1 min with 180 µl SB17T. All capture beads for each protein were pooled and the volume brought to 1.7 ml with SB17T. For the binding assay, 50 µl of pooled capture beads were dispensed into the wells of a pre-wet MSBVN12 filter plate, using duplicate wells for each aptamer to be tested as detection agent, and mixed with 50 µl of 20 nM protein in SB17T+1% BSA or 50 µl buffer for the no-protein controls. After at least 30 min with shaking at 1100 rpm, the plate was vacuum-washed 2×1 min with 180 µl SB17T+1% BSA and the beads were resuspended in 50 µl SB17T+BSA. Heat-cooled detection aptamers were added to individual wells, using 50 µl of 12.5 nM stocks, and incubation was continued for 30 min with shaking, then the beads were washed and resuspended as above. As a reporter, 50 µl of 10 µg/ml streptavidin-phycoerythrin (SA-PE) conjugate (Moss, Pasadena, Md., USA, Cat. No. SAPE-001) in SB17T+BSA were added, and the beads were again shaken, washed, and resuspended as above. The plate was read on a Luminex 100 analyzer (time out: enabled 120 s, DD gating: 7500-8000, reporter gain: high PMT).

Sandwich Assay Target Titrations.

Binding curves for AB-H aptamer pairs were generated for both a bead-based and plate-based sandwich assay. For the bead-assay, a single LumAvidin microsphere bead type carrying one specific capture aptamer was used, and the assay was performed essentially as described for the screening assay above, except that target protein was added in half-log serial dilutions starting at 100 nM to obtain 12-point binding curves. For the plate-assay, 2 pmol (100 µl of 20 nM) heat-cooled aptamers were immobilized overnight on Reacti-Bind Streptavidin Coated Plates (Pierce Biotechnology-Thermo Scientific, Rockford, Ill., USA, Cat. No. 15500). The wells were washed for 5 min each with 100 µl 50 nM streptavidin and with 10 mM biotin in SB17T, then blocked with 200 µl SB17T+1% BSA for 10 min. Target proteins were added and incubated for 45 min with shaking, and the plate was washed 2×1 min with 150 µl SB17T+1% BSA. Detection aptamers were added (100 µl of 20 nM stocks in SB17T+1% BSA), incubation was continued for 35 minutes, and the wells washed as above. As reporter, 100 µl of 0.4 µg/ml SA-HRP conjugate (Life Technologies, Carlsbad, Calif., USA, Cat. No. S-911) was added for 35 minutes with shaking, followed by three washes with SB17 (no Tween-20). TMB substrate (FisherScientific, Pittsburgh, Pa., USA, Cat. No. PI34028) was added (100 µl) for 20-30 min, then the reaction was stopped with 50 µl of 10% sulfuric acid, and absorbance at 450 nm was recorded.

Example 2: Selection and Identification of Aptamer Pairs for Binary Toxin A Chain (CdtA) of *Clostridium Difficile*

This example provides the representative method for the selection and production of DNA aptamer pairs for the binary toxin A chain (CdtA) protein of *C. difficile*. This representative method is outlined in FIG. 1 and may be used to identify aptamer pairs for other targets (e.g., protein) of interest.

SELEX with purified recombinant CdtA protein and a TrpdU-modified library yielded clone 4758-6 having a $K_d$ of 0.86 nM. The nucleic acid molecule of clone 4758-6 is as an aptamer forty (40) nucleotides in length comprising C-5 modified pyrimidines, specifically TrpdU, and is capable of binding to the CdtA protein. The nucleotide sequence is as follows: 5'-

(SEQ ID NO: 1)
GAAGACTTTAATTCTGACATGGTGTCCAATGGCGCGCGAG-3', with T represents a TrpdU. In an attempt to identify a non-competing aptamer, CdtA in a complex with a non-amplifiable version of clone 4758-6 (CdtA-4758-6 aptamer complex) was used as the target in a second SELEX (pool 5579-2NapdU modified aptamer library), which employed a 2NapdU-modified library instead of the TrpdU library used to generate the 4758-6 clone. Table 1 below provides a summary of the sequence analysis of the aptamers (or clones) identified in SELEX using the 4758-6 aptamer clone complexed with the CdtA protein, the corresponding number of sequence patterns identified ("#"), $K_d$ data and whether a aptamer-sandwich formed with the CdtA-4758-6 aptamer complex ("Sandwich"). Abbreviations: free protein (F.P.) and competitor (Comp.).

TABLE 1

CdtA-4758-6 complex SELEX pool 5579 (2NapdU mod.) (n = 45 evaluable sequences)

| # | Clone ID | $K_d$ (nM) F.P. | $K_d$ (nM) w/Comp. | Sandwich |
|---|---|---|---|---|
| 20 | 5579-12 | 0.97 | 0.28 | Yes |
| 4 | 5579-5 | 2.24 | 0.21 | Yes |
| 12 | 5579-11 | 0.07 | 0.71 | No |
| 5 | 5579-8 | 0.53 | 0.55 | Yes |
| 2 | 5579-10 | 0.15 | 0.13 | Yes |
| 2 | NT[2] | NT | NT | NT |

[2]NT, not tested

*eDNA full-length SOMAmer testing data (no synthetic SOMAmers produced)

SELEX with free CdtA (pool 5551) was done in parallel with the same 2NapdU library used in SELEX against the CdtA-4758-6 aptamer complex, and also with a different PEdU modified library (pool 5574). Following eight rounds of selection, all SELEX experiments were successful in generating sequence pools with at least 100-fold affinity enrichment compared to starting random libraries. Table 2 below provides a summary of the sequence analysis of the aptamers (or clones) identified in SELEX using the free CdtA protein (pool 5551-2NapdU modified aptamer library), the corresponding number of sequence patterns identified ("#"), $K_d$ data and whether a aptamer-sandwich formed ("Sandwich").

TABLE 2

Free CdtA SELEX pool 5551 (2NapdU mod.) (n = 43 evaluable sequences)

| # | Clone ID | $K_d$ (nM) F.P. | $K_d$ (nM) w/Comp. | Sandwich |
|---|---|---|---|---|
| 6 | 5551-81 | 0.54 | 0.55 | Yes |
| 4 | 5551-50 | 0.09 | 17.60 | No |
| 15 | 5551-52 | 0.14 | 0.22 | No |
| 8 | 5551-51 | Bead binder | NT | NT |
| 5 | 5551-49 | 0.31 | 20.60 | No |
| 2 | 5551-76 | NT | NT | NT |
| 2 | 5551-82 | NT | NT | NT |
| 1 | NT | NT | NT | NT |

[2]NT, not tested

*eDNA full-length SOMAmer testing data (no synthetic SOMAmers produced)

Table 3 below provides a summary of the sequence analysis of the aptamers (or clones) identified in SELEX using the free CdtA protein (pool 5574—PEdU modified aptamer library), the corresponding number of sequence patterns identified ("#"), $K_d$ data and whether a aptamer-sandwich formed ("Sandwich").

TABLE 3

Free CdtA SELEX pool 5574 (PEdU mod)
(n = 41 evaluable sequences)

| # | Clone ID | $K_d$ (nM) F.P. | $K_d$ (nM) w/Comp. | Sandwich |
|---|---|---|---|---|
| 13 | 5574-49 | 1.5 | >10 | No |
| 11 | 5574-56 | 2.92* | >10 | No |
| 10 | 5574-51 | >10* | >10 | NT |
| 2 | 5574-67 | 4.20* | >10 | NT |
| 2 | 5574-83 | 4.66* | >10 | NT |
| 3 | NT | NT | NT | NT |

²NT, not tested
*eDNA full-length SOMAmer testing data (no synthetic SOMAmers produced)

Comparative sequence analysis of the 2NapdU clones from affinity-enriched pools 5579 (CdtA-4758-6; Table 1) and 5551 (free CdtA; Table 2) revealed differences in the patterns and abundance, but there were some shared sequence motifs as well (FIG. 1B). The dominant pattern occurred in 20 (44%) of the sequences in pool 5579, but only in 5 (12%) of the sequences in pool 5551. Sequences harboring this pattern (e.g., 5579-7, 5579-12, 5579-21) performed consistently well in sandwich format with the original ligand 4758-6. Another pattern and two sequences found in multiple copies, were found exclusively in pool 5579 (CdtA-4758-6), and also these sequences were non-competing with 4758-6. Another pattern was present in sequences from both pools, and this family contained the most active aptamers (e.g. 5579-11), but they failed in the sandwich assay. Most likely, these sequences successfully competed with 4758-6 during SELEX, occupying the same epitope with higher affinity or superior binding kinetics.

Two different patterns and three multicopy sequences were found only in pool 5551 (free CdtA SELEX) and failed the sandwich assay. Finally, none of the sequences generated in free CdtA SELEX using a PEdU library bound the complex, although several of them had sub-nanomolar affinity to free CdtA. Thus, SELEX with the CdtA-4758-6 complex clearly resulted in a higher fraction of sequences useful for sandwich assays in conjunction with 4758-6, although free CdtA SELEX also produced a few new aptamers that bound to a different epitope.

Figure 1B:
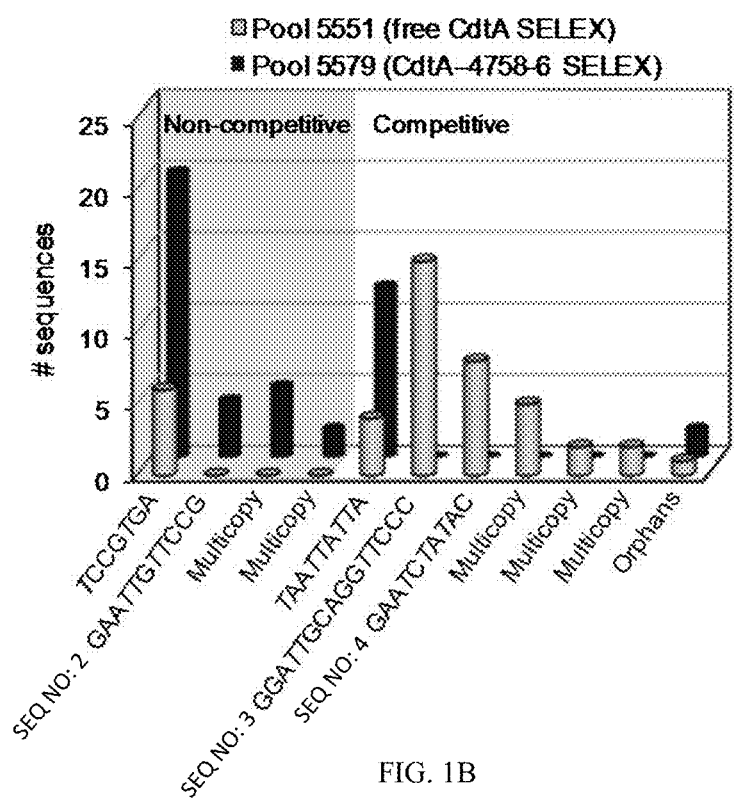
FIG. 1B shows a representation of sequence patterns and multicopy sequences selected with free CdtA protein (pool 5551) or with CdtA-4758-6 complex (pool 5579); T=2NapdU. Non-competitive binding with the first CdtA aptamer, 4758-6, is indicated by shading.
Figure 1F:
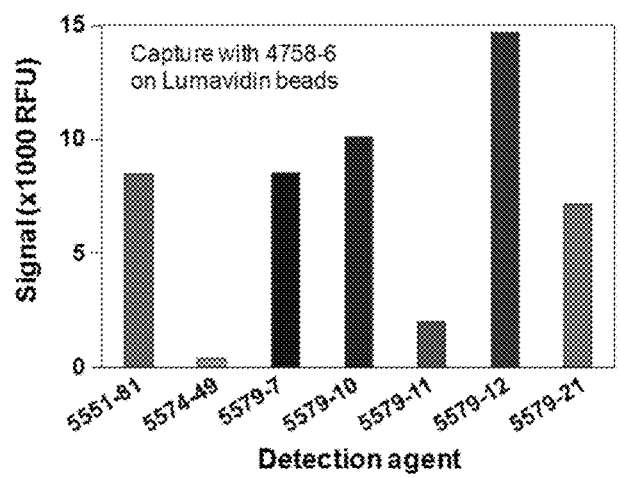
FIG. 1F shows screening for aptamer pairs on the Luminex platform using 4758-6 as capture agent bound to LumAvidin beads, and individual aptamers as detection agents. All aptamers were made synthetically as 50-mers and contained a single biotin at their 5'-end to allow their immobilization on the beads, which were then blocked from further binding with 1 mM biotin, and to allow detection with a streptavidin-phycoerythrin conjugate.
Figure 1G:
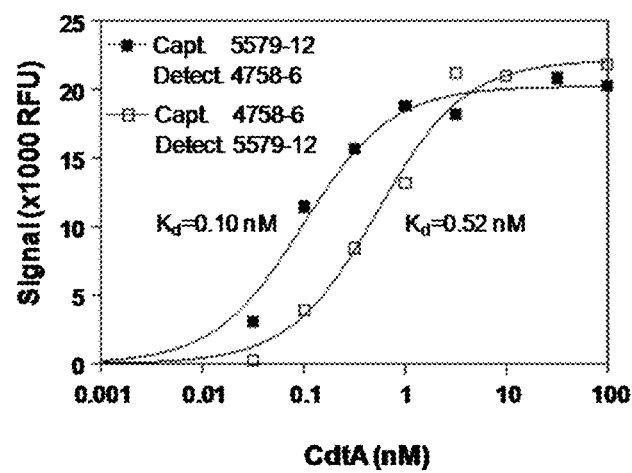
FIG. 1G shows CdtA sandwich assay with 4758-6 (25 nM) as capture agent and 5579-12 (10 nM) as detection agent, or switching the two reagents.

The new aptamers bound the free protein with affinities ranging from 0.05 nM-14 nM (FIG. 1C), and were also tested in competition assays and in sandwich format together with the existing 4758-6 TrpdU aptamer (FIGS. 1D and 1E). As shown for clone 5579-12, which possessed affinity comparable to 4758-6 ($K_d$=0.67 nM vs 0.86 nM), binding to CdtA was not affected by the presence of a ~100-fold excess (10 nM) 4758-6 competitor, or when 4758-6 was used as a capture agent, indicating that the two sequences bind to distinct CdtA epitopes. In contrast, binding of aptamer 5579-11, which had superior affinity compared to 4758-6 ($K_d$=0.05 nM vs 0.86 nM), was reduced with 4758-6 as competitor or capture agent. Representative sequences from each SELEX were also screened on the Luminex platform, where the first aptamer 4758-6 served as capture agent on beads. Most clones from complex SELEX (5579-7, 5579-10, 5579-12, 5579-21) as well as one clone from free CdtA SELEX (5551-81) confirmed their binding when used as detection agent (FIG. 1F). Capture and detection agents were interchangeable for 4758-6 and 5579-12, producing similar binding curves in the Luminex sandwich assay (FIG. 1G).

Example 3: Selection of Aptamer Pairs for Eight Different Protein Targets

This example provides the representative method for the selection and production of DNA aptamer pairs for the following protein targets: angiopoietin-2 (ANGPT2), thrombospondin-2 (TSP2), chordin-like 1 (CRDL1), matrilin-2 (MATN2), glycoprotein VI (GPVI), endothelial cell-selective adhesion molecule (ESAM), complement 7 (C7), and plasminogen (PLG).

A two-tiered strategy was employed to obtain aptamer pairs to the target proteins. For the first strategy, aptamers obtained via SELEX that demonstrated good affinity ($K_d$<10 nM) yielded functional aptamer pairs for three of the eight targets (C7, MATN2, PLG), all with BndU as the modified nucleotide. For the second strategy, SELEX was performed with target-SOMAmer complexes, employing two new modified nucleotide libraries (TrpdU and 2NapdU), and, in parallel a free protein SELEX using either a TrpdU or 2NapdU library. After seven rounds of SELEX, all 24 pools showed convergence based on DNA reassociation ($C_0t$) kinetics and demonstrated low-nanomolar or sub-nanomolar $K_d$ values. Cloning and routine sequencing of at least 48 SOMAmers per pool allowed comparative analysis of sequences obtained in SELEX with protein-SOMAmer complex and free protein targets. In all cases, active clones that bound the protein-SOMAmer complexes were obtained, however, a larger fraction of the tested clones did not bind the complex where the free target was used for SELEX. Therefore, using protein-SOMAmer complex targets during SELEX clearly increased the likelihood of finding sandwich candidates. An exception, however, were clones from pool 7565 TrpdU selected with the ESAM-2981-9 complex, all of which shared a common sequence pattern and showed binding of the ESAM-2981-9 complex but not free ESAM protein. These sequences were later shown to interact with SOMAmer 2981-9 rather than bind the target protein.

Figure 2A:
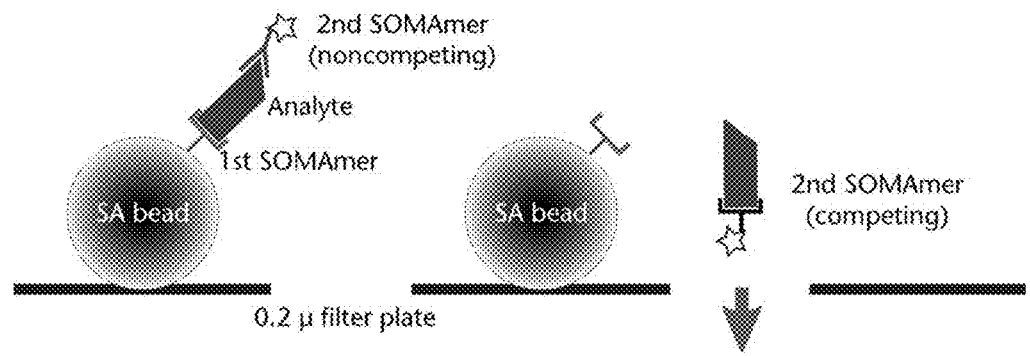
FIG. 2A shows an equilibrium binding assay to screen for individual aptamer sandwich pairs, using biotinylated capture aptamers on streptavidin beads and radiolabeled detection aptamers.

The observed binding of the new clones to the protein-menu SOMAmer complexes did not prove the existence of a true sandwich, since they might simply displace the menu SOMAmer and bind to the same epitope. To make this distinction, the new clones were subjected to binding assays in the presence of 10 nM (~100-fold) excess unlabeled competitor menu SOMAmer and in sandwich assays with the menu SOMAmers as capture agents. The sandwich assay depicted in FIG. 2A results in a signal only if a sandwich is formed, but not if displacement of the first SOMAmer occurs. Detailed sequence analysis and binding characteristics for all SOMAmers (synthetic 5'AB-H 50mers) obtained in the SELEX with complexed or free proteins are shown below in Tables 4-27.

Tables 4-6 provide a summary for the aptamers to the angiopoietin-2 (ANGPT2) protein. The nucleic acid molecule of clone 2602-2 is as an aptamer forty (40) nucleotides in length comprising C-5 modified pyrimidines, specifically BndU, and is capable of binding to the ANGPT2 protein.

TABLE 4

ANGPT2-2602-2 complex SELEX pool 7560 (TrpdU mod.)
(n = 43 evaluable sequences)

| # | Clone ID | $K_d$ (nM) F.P. | $K_d$ (nM) w/Comp. | Sandwich |
|---|---|---|---|---|
| 26 | 7560-4 | 0.29 | 0.59 | Yes |
| 4 | 7560-1 | 0.19 | 1.26 | Yes |
| 4 | 7560-19 | 6.35 | 2.65 | Yes |

TABLE 4-continued

ANGPT2-2602-2 complex SELEX pool 7560 (TrpdU mod.)
(n = 43 evaluable sequences)

| # | Clone ID | $K_d$ (nM) F.P. | $K_d$ (nM) w/Comp. | Sandwich |
|---|---|---|---|---|
| 2 | 7560-27 | >100* | NT | NT |
| 7 | NT | NT | NT | NT |

[2]NT, not tested
*eDNA full-length SOMAmer testing data (no synthetic SOMAmers produced)

TABLE 5

Free ANGPT2 SELEX pool 7568 (TrpdU mod.)
(n = 80 evaluable sequences)

| # | Clone ID | $K_d$ (nM) F.P. | $K_d$ (nM) w/Comp. | Sandwich |
|---|---|---|---|---|
| 29 | 7568-4 | 0.88* | NT | NT |
| 4 | 7568-87 | NT | NT | NT |
| 15 | 7568-30 | 0.15 | 0.15 | Yes |
| 4 | 7568-29 | 0.50 | 1.05 | Yes |
| 4 | 7568-53 | 0.78 | 0.65 | Yes |
| 2 | 7568-1 | 3.14 | 5.24 | Yes |
| 2 | 7568-12 | >100* | NT | NT |
| 2 | 7568-14 | 6.84* | NT | NT |
| 2 | 7568-15 | NT | NT | NT |
| 2 | 7568-25 | NT | NT | NT |
| 14 | NT | NT | NT | NT |

[2]NT, not tested
*eDNA full-length SOMAmer testing data (no synthetic SOMAmers produced)

TABLE 6

ANGPT2-2602-2 complex SELEX pool 7573 (2NapdU mod.)
(n = 42 evaluable sequences)

| # | Clone ID | $K_d$ (nM) F.P. | $K_d$ (nM) w/Comp. | Sandwich |
|---|---|---|---|---|
| 9 | 7573-14 | 0.21 | 0.22 | Yes |
| 4 | 7573-6 | >10 | NT | NT |
| 2 | 7573-15 | 0.82 | 0.98 | Yes |
| 8 | 7573-1 | 0.12 | 0.17 | Yes |
| 3 | 7573-42 | 0.07 | 0.09 | Yes |
| 3 | 7573-21 | 0.16 | 0.54 | Yes |
| 3 | 7573-22 | 1.5 | NT | NT |
| 2 | 7573-12 | NT | NT | NT |
| 8 | NT | NT | NT | NT |

[2]NT, not tested
*eDNA full-length SOMAmer testing data (no synthetic SOMAmers produced)

Tables 7-9 provide a summary for the aptamers to the thrombospondin-2 (TSP2) protein. The nucleic acid molecule of clone 3339-33 is as an aptamer forty (40) nucleotides in length comprising C-5 modified pyrimidines, specifically BndU, and is capable of binding to the TSP2 protein.

TABLE 7

TSP2-3339-33
complex SELEX pool 7561 (TrpdU mod.)
(n = 41 evaluable sequences)

| # | Clone ID | $K_d$ (nM) F.P. | $K_d$ (nM) w/Comp. | Sandwich |
|---|---|---|---|---|
| 8 | 7561-59 | 0.19 | 0.14 | Yes |
| 5 | 7561-69 | NT | NT | NT |
| 9 | 7561-55 | 0.04 | 0.04 | Yes |
| 3 | 7561-49 | NT | NT | NT |

TABLE 7-continued

TSP2-3339-33
complex SELEX pool 7561 (TrpdU mod.)
(n = 41 evaluable sequences)

| # | Clone ID | $K_d$ (nM) F.P. | $K_d$ (nM) w/Comp. | Sandwich |
|---|---|---|---|---|
| 2 | 7561-83 | 0.02 | 0.05 | Yes |
| 7 | 7561-65 | 0.09 | 3.08 | No |
| 7 | NT | NT | NT | NT |

[2]NT, not tested
*eDNA full-length SOMAmer testing data (no synthetic SOMAmers produced)

TABLE 8

Free TSP2 SELEX pool 7569 (TrpdU mod.)
(n = 43 evaluable sequences)

| # | Clone ID | $K_d$ (nM) F.P. | $K_d$ (nM) w/Comp. | Sandwich |
|---|---|---|---|---|
| 3 | 7569-1 | NT | NT | NT |
| 5 | 7569-23 | NT | NT | NT |
| 5 | 7569-29 | 0.03 | 0.04 | Yes |
| 5 | 7569-22 | 0.43 | 3.10 | Yes |
| 5 | 7569-18 | 0.05* | 0.13* | NT |
| 3 | 7569-33 | NT | NT | NT |
| 3 | 7569-45 | NT | NT | NT |
| 2 | 7569-6 | 0.19 | 0.25 | NT |
| 2 | 7569-16 | NT | NT | NT |
| 10 | NT | NT | NT | NT |

[2]NT, not tested
*eDNA full-length SOMAmer testing data (no synthetic SOMAmers produced)

TABLE 9

TSP2-3339-33 complex SELEX pool 7574 (2NapdU mod.)
(n = 42 evaluable sequences)

| # | Clone ID | $K_d$ (nM) F.P. | $K_d$ (nM) w/Comp. | Sandwich |
|---|---|---|---|---|
| 11 | 7574-62 | 0.09 | 0.08 | Yes |
| 20 | 7574-57 | 0.03 | 0.08 | Yes |
| 5 | 7574-53 | 0.08 | 0.07 | Yes |
| 3 | 7574-64 | 0.18 | 1.10 | Yes |
| 3 | NT | NT | NT | NT |

[2]NT, not tested
*eDNA full-length SOMAmer testing data (no synthetic SOMAmers produced)

Tables 10-12 provide a summary for the aptamers to the chordin-like 1 (CRDL1) protein. The nucleic acid molecule of clone 3362-61 is as an aptamer forty (40) nucleotides in length comprising C-5 modified pyrimidines, specifically BndU, and is capable of binding to the CRDL1 protein.

TABLE 10

CRDL1-3362-61
complex SELEX pool 7562 (TrpdU mod.)
(n = 47 evaluable sequences)

| # | Clone ID | $K_d$ (nM) F.P. | $K_d$ (nM) w/Comp. | Sandwich |
|---|---|---|---|---|
| 4 | 7562-3 | 0.13 | 0.23 | Yes |
| 4 | 7562-24 | 0.34 | 0.23 | Yes |
| 4 | 7562-8 | 0.38 | 0.31 | Yes |
| 5 | 7562-4 | NT | NT | NT |
| 5 | 7562-23 | 0.68 | 0.38 | Yes |
| 2 | 7562-6 | 0.44 | 0.17 | Yes |
| 3 | 7562-12 | 0.12 | 0.49 | Yes |
| 3 | 7562-31 | 0.26 | 0.17 | Yes |

TABLE 10-continued

CRDL1-3362-61 complex SELEX pool 7562 (TrpdU mod.)
(n = 47 evaluable sequences)

| # | Clone ID | $K_d$ (nM) F.P. | $K_d$ (nM) w/Comp. | Sandwich |
|---|---|---|---|---|
| 2 | 7562-2 | 0.28 | 0.13 | Yes |
| 2 | 7562-7 | 1.52 | 0.23 | Yes |
| 2 | 7562-19 | 0.29 | 0.27 | Yes |
| 11 | NT | NT | NT | NT |

[2]NT, not tested
*eDNA full-length SOMAmer testing data (no synthetic SOMAmers produced)

TABLE 11

Free CRDL1 SELEX pool 7570 (TrpdU mod.)
(n = 41 evaluable sequences)

| # | Clone ID | $K_d$ (nM) F.P. | $K_d$ (nM) w/Comp. | Sandwich |
|---|---|---|---|---|
| 2 | 7570-90 | NT | NT | NT |
| 1 | 7570-64 | NT | NT | NT |
| 4 | 7570-67 | 0.30* | 0.28* | NT |
| 6 | 7570-50 | 0.50* | 2.44* | NT |
| 5 | 7570-52 | 0.89* | 2.14* | NT |
| 2 | 7570-57 | 0.74* | 3.13* | NT |
| 4 | 7570-55 | 0.40 | 0.13 | Yes |
| 2 | 7570-53 | 0.41* | 1.07* | NT |
| 2 | 7570-84 | NT | NT | NT |
| 13 | NT | NT | NT | NT |

[2]NT, not tested
*eDNA full-length SOMAmer testing data (no synthetic SOMAmers produced)

TABLE 12

CRDL1-3362-61 complex SELEX pool 7575 (2NapdU mod.)
(n = 42 evaluable sequences)

| # | Clone ID | $K_d$ (nM) F.P. | $K_d$ (nM) w/Comp. | Sandwich |
|---|---|---|---|---|
| 9 | 7575-2 | 0.38 | 0.19 | Yes |
| 7 | 7575-6 | 0.41 | 0.43 | Yes |
| 5 | 7575-19 | 3.51 | 0.13 | Yes |
| 2 | 7575-5 | 0.30 | 0.19 | Yes |
| 3 | 7575-3 | 0.55 | 3.36 | NT |
| 16 | NT | NT | NT | NT |

[2]NT, not tested
*eDNA full-length SOMAmer testing data (no synthetic SOMAmers produced)

Tables 13-15 provide a summary for the aptamers to the matrilin-2 (MATN2) protein. The nucleic acid molecule of clone 3325-2 is as an aptamer forty (40) nucleotides in length comprising C-5 modified pyrimidines, specifically BndU, and is capable of binding to the MATN2 protein.

TABLE 13

MATN2-3325-2 complex SELEX pool 7563 (TrpdU mod.)
(n = 40 evaluable sequences)

| # | Clone ID | $K_d$ (nM) F.P. | $K_d$ (nM) w/Comp. | Sandwich |
|---|---|---|---|---|
| 4 | 7563-61 | NT | NT | NT |
| 10 | 7563-63 | 0.17* | 13.6* | NT |
| 8 | 7563-60 | 12.20 | 0.78 | Yes |
| 3 | 7563-51 | 3.11 | 1.19 | NT |
| 3 | 7563-55 | NT | NT | NT |
| 2 | 7563-56 | >10* | 1.75* | NT |

TABLE 13-continued

MATN2-3325-2 complex SELEX pool 7563 (TrpdU mod.)
(n = 40 evaluable sequences)

| # | Clone ID | $K_d$ (nM) F.P. | $K_d$ (nM) w/Comp. | Sandwich |
|---|---|---|---|---|
| 2 | 7563-58 | NT | NT | NT |
| 8 | NT | NT | NT | NT |

[2]NT, not tested
*eDNA full-length SOMAmer testing data (no synthetic SOMAmers produced)

TABLE 14

Free MATN2 SELEX pool 7571 (TrpdU mod.)
(n = 46 evaluable sequences)

| # | Clone ID | $K_d$ (nM) F.P. | $K_d$ (nM) w/Comp. | Sandwich |
|---|---|---|---|---|
| 5 | 7571-11 | 0.66* | 15.4* | NT |
| 2 | 7571-31 | 5.31 | 3.65 | Yes |
| 4 | 7571-20 | 1.18 | 0.96 | Yes |
| 4 | 7571-1 | 0.33* | >10* | NT |
| 4 | 7571-12 | 3.99* | >10* | NT |
| 27 | NT | NT | NT | NT |

[2]NT, not tested
*eDNA full-length SOMAmer testing data (no synthetic SOMAmers produced)

TABLE 15

MATN2-3352-2 complex SELEX pool 7576 (2NapdU mod.)
(n = 90 evaluable sequences)

| # | Clone ID | $K_d$ (nM) F.P. | $K_d$ (nM) w/Comp. | Sandwich |
|---|---|---|---|---|
| 31 | 7576-61 | 0.63 | 0.49 | Yes |
| 10 | 7576-40 | 2.70 | 1.70 | No |
| 3 | 7576-13 | 0.94* | 1.40* | NT |
| 11 | 7576-11 | >100 | 6.53 | Yes |
| 5 | 7576-64 | 1.33 | 0.83 | No |
| 4 | 7576-19 | 4.57 | 2.08 | Yes |
| 4 | 7576-30 | 5.00 | 3.79 | Yes |
| 2 | 7576-51 | 0.30 | 0.46 | Yes |
| 20 | NT | NT | NT | NT |

[2]NT, not tested
*eDNA full-length SOMAmer testing data (no synthetic SOMAmers produced)

Tables 16-18 provide a summary for the aptamers to the glycoprotein VI (GPVI) protein. The nucleic acid molecule of clone 3194-36 is as an aptamer forty (40) nucleotides in length comprising C-5 modified pyrimidines, specifically BndU, and is capable of binding to the GPVI protein.

TABLE 16

GPVI-3194-36 complex SELEX pool 7564 (TrpdU mod.)
(n = 82 evaluable sequences)

| # | Clone ID | $K_d$ (nM) F.P. | $K_d$ (nM) w/Comp. | Sandwich |
|---|---|---|---|---|
| 24 | 7564-5 | 0.04 | 0.02 | Yes |
| 20 | 7564-29 | 0.02* | 0.35* | Yes |
| 8 | 7564-18 | 0.08 | 0.12 | No |
| 8 | 7564-3 | 0.07 | 0.18 | No |
| 2 | 7564-153 | NT | NT | NT |
| 9 | 7564-174 | 0.04 | 0.42 | NT |
| 5 | 7564-13 | NT | NT | NT |
| 6 | NT | NT | NT | NT |

[2]NT, not tested
*eDNA full-length SOMAmer testing data (no synthetic SOMAmers produced)

TABLE 17

Free GPVI SELEX pool 7572 (TrpdU mod.)
(n = 44 evaluable sequences)

| # | Clone ID | $K_d$ (nM) F.P. | $K_d$ (nM) w/Comp. | Sandwich |
|---|---|---|---|---|
| 6 | 7572-68 | NT | NT | NT |
| 6 | 7572-61 | NT | NT | NT |
| 2 | 7572-70 | NT | NT | NT |
| 7 | 7572-60 | 0.12 | >10 | NT |
| 4 | 7572-79 | 0.03 | 1.83 | NT |
| 2 | 7572-49 | NT | NT | NT |
| 17 | NT | NT | NT | NT |

[2]NT, not tested
*eDNA full-length SOMAmer testing data (no synthetic SOMAmers produced)

TABLE 18

GPVI-3194-36 complex SELEX pool 7577 (2NapdU mod.)
(n = 44 evaluable sequences)

| # | Clone ID | $K_d$ (nM) F.P. | $K_d$ (nM) w/Comp. | Sandwich |
|---|---|---|---|---|
| 4 | 7577-51 | >10 | 0.10 | Yes |
| 7 | 7577-70 | >10 | 1.32 | NT |
| 4 | 7577-49 | >32 | 13.3 | NT |
| 6 | 7577-65 | NT | NT | NT |
| 3 | 7577-50 | 0.04 | 0.92 | No |
| 20 | NT | NT | NT | NT |

[2]NT, not tested
*eDNA full-length SOMAmer testing data (no synthetic SOMAmers produced)

Tables 19-21 provide a summary for the aptamers to the endothelial cell-selective adhesion molecule (ESAM) protein. The nucleic acid molecule of clone 2981-9 is as an aptamer forty (40) nucleotides in length comprising C-5 modified pyrimidines, specifically BndU, and is capable of binding to the ESAM protein.

TABLE 19

ESAM-2981-9 complex SELEX pool 7565 (T = TrpdU)
(n = 44 evaluable sequences)

| # | Clone ID | $K_d$ (nM) F.P. | $K_d$ (nM) w/Comp. | Sandwich |
|---|---|---|---|---|
| 33 | 7565-67 | >10 | 0.53 | No |
| 7 | 7565-54 | >10 | 4.40 | No |
| 4 | NT | NT | NT | NT |

[2]NT, not tested
*eDNA full-length SOMAmer testing data (no synthetic SOMAmers produced)

TABLE 20

ESAM-2981-9 complex SELEX pool 7578 (T = 2NapdU)
(n = 42 evaluable sequences)

| # | Clone ID | $K_d$ (nM) F.P. | $K_d$ (nM) w/Comp. | Sandwich |
|---|---|---|---|---|
| 9 | 7578-5 | 0.18 | 0.43 | No |
| 8 | 7578-34 | >10 | 0.56 | No |
| 8 | 7578-22 | >10 | 1.57 | NT |
| 3 | 7578-3 | 0.37 | 15.3 | NT |
| 2 | 7578-11 | 0.45 | 4.54 | NT |
| 12 | NT | NT | NT | NT |

[2]NT, not tested
*eDNA full-length SOMAmer testing data (no synthetic SOMAmers produced)

TABLE 21

Free ESAM SELEX pool 7581 (T = 2NapdU)
(n = 85 evaluable sequences)

| # | Clone ID | $K_d$ (nM) F.P | $K_d$ (nM) w/Comp. | Sandwich |
|---|---|---|---|---|
| 1 | 7581-2 | NT | NT | NT |
| 3 | 7581-42 | NT | NT | NT |
| 12 | 7581-41 | 0.03 | 0.06 | No |
| 9 | 7581-5 | 0.48 | 3.58 | NT |
| 13 | 7581-8 | 0.44 | 3.55 | NT |
| 10 | 7581-3 | 0.40 | 2.32 | NT |
| 7 | 7581-54 | 0.24 | 3.00 | NT |
| 4 | 7581-9 | 0.16 | 1.99 | NT |
| 26 | NT | NT | NT | NT |

[2]NT, not tested
*eDNA full-length SOMAmer testing data (no synthetic SOMAmers produced)

Tables 22-24 provide a summary for the aptamers to the complement 7 (C7) protein. The nucleic acid molecule of clone 2888-49 is as an aptamer forty (40) nucleotides in length comprising C-5 modified pyrimidines, specifically BndU, and is capable of binding to the C7 protein.

TABLE 22

C7-2888-49 complex SELEX pool 7566 (TrpdU mod.)
(n = 46 evaluable sequences)

| # | Clone ID | $K_d$ (nM) F.P | $K_d$ (nM) w/Comp. | Sandwich |
|---|---|---|---|---|
| 6 | 7566-14 | 47.0 | 5.04 | Yes |
| 4 | 7566-40 | 0.14* | 0.05* | No |
| 18 | 7566-22 | >10 | Bead binder | NT |
| 2 | 7566-29 | 13.3 | 10.4 | NT |
| 16 | NT | NT | NT | NT |

[2]NT, not tested
*eDNA full-length SOMAmer testing data (no synthetic SOMAmers produced)

TABLE 23

C7-2888-49 complex SELEX pool 7579 (2NapdU mod.)
(n = 43 evaluable sequences)

| # | Clone ID | $K_d$ (nM) F.P | $K_d$ (nM) w/Comp. | Sandwich |
|---|---|---|---|---|
| 2 | 7579-65 | 0.76* | 0.04* | Yes |
| 2 | 7579-67 | 0.40* | 0.09* | Yes |
| 9 | 7579-82 | NT | NT | NT |
| 1 | 7579-68 | >10 | >10 | NT |
| 8 | 7579-88 | 0.19 | 0.17 | No |
| 3 | 7579-64 | 0.22 | 0.13 | No |
| 2 | 7579-85 | 13.2 | 13.8 | NT |
| 16 | NT | NT | NT | NT |

[2]NT, not tested
*eDNA full-length SOMAmer testing data (no synthetic SOMAmers produced)

TABLE 24

Free C7 SELEX pool 7582 (2NapdU mod.)
(n = 42 evaluable sequences)

| # | Clone ID | $K_d$ (nM) F.P | $K_d$ (nM) w/Comp. | Sandwich |
|---|---|---|---|---|
| 2 | 7582-52 | NT | NT | NT |
| 22 | 7582-56 | >10 | >10 | NT |
| 2 | NT | NT | NT | NT |
| 5 | 7582-67 | NT | NT | NT |

TABLE 24-continued

Free C7 SELEX pool 7582 (2NapdU mod.)
(n = 42 evaluable sequences)

| # | Clone ID | $K_d$ (nM) F.P | $K_d$ (nM) w/Comp. | Sandwich |
|---|---|---|---|---|
| 2 | 7582-52 | NT | NT | NT |
| 9 | NT | NT | NT | NT |

²NT, not tested
*eDNA full-length SOMAmer testing data (no synthetic SOMAmers produced)

Tables 25-27 provide a summary for the aptamers to the plasminogen (PLG) protein. The nucleic acid molecule of clone 4151-6 is as an aptamer forty (40) nucleotides in length comprising C-5 modified pyrimidines, specifically BndU, and is capable of binding to the PLG protein.

TABLE 25

PLG-4151-6 complex SELEX pool 7567 (TrpdU mod.)
(n = 42 evaluable sequences)

| # | Clone ID | $K_d$ (nM) F.P | $K_d$ (nM) w/Comp. | Sandwich |
|---|---|---|---|---|
| 12 | 7567-53 | >10 | Bead binder | NT |
| 5 | 7567-63 | 2.41 | 1.95 | NT |
| 3 | 7567-95 | >10 | Bead binder | NT |
| 2 | 7567-64 | 0.99 | 0.30 | Yes |
| 20 | NT | NT | NT | NT |

²NT, not tested
*eDNA full-length SOMAmer testing data (no synthetic SOMAmers produced)

TABLE 26

PLG-4151-6 complex SELEX pool 7580 (2NapdU mod.)
(n = 42 evaluable sequences)

| # | Clone ID | $K_d$ (nM) F.P | $K_d$ (nM) w/Comp. | Sandwich |
|---|---|---|---|---|
| 1 | 7580-16 | NT | NT | NT |
| 2 | 7580-35 | NT | NT | NT |
| 1 | 7580-17 | NT | NT | NT |
| 2 | 7580-19 | 0.77 | 1.14 | Yes |
| 2 | 7580-13 | 1.75 | 1.37 | Yes |
| 11 | 7580-4 | >10 | Bead binder | NT |
| 7 | 7580-43 | 1.89 | 1.51 | NT |
| 16 | NT | NT | NT | NT |

²NT, not tested
*eDNA full-length SOMAmer testing data (no synthetic SOMAmers produced)

TABLE 27

Free PLG SELEX pool 7583 (2NapdU mod.)
(n = 43 evaluable sequences)

| # | Clone ID | $K_d$ (nM) F.P | $K_d$ (nM) w/Comp. | Sandwich |
|---|---|---|---|---|
| 3 | 7583-19 | 3.72 | 0.72 | Yes |
| 8 | 7583-8 | 1.95* | 0.86* | NT |
| 3 | 7583-7 | 3.91* | 2.30* | NT |
| 2 | 7583-15 | 1.14 | 0.21 | Yes |
| 2 | 7583-3 | 0.81 | 0.30 | Yes |
| 2 | 7583-24 | 8.72 | 0.59 | Yes |
| 2 | 7583-12 | 1.94* | 1.69* | NT |
| 21 | NT | NT | NT | NT |

²NT, not tested
*eDNA full-length SOMAmer testing data (no synthetic SOMAmers produced)

Figure 2B:
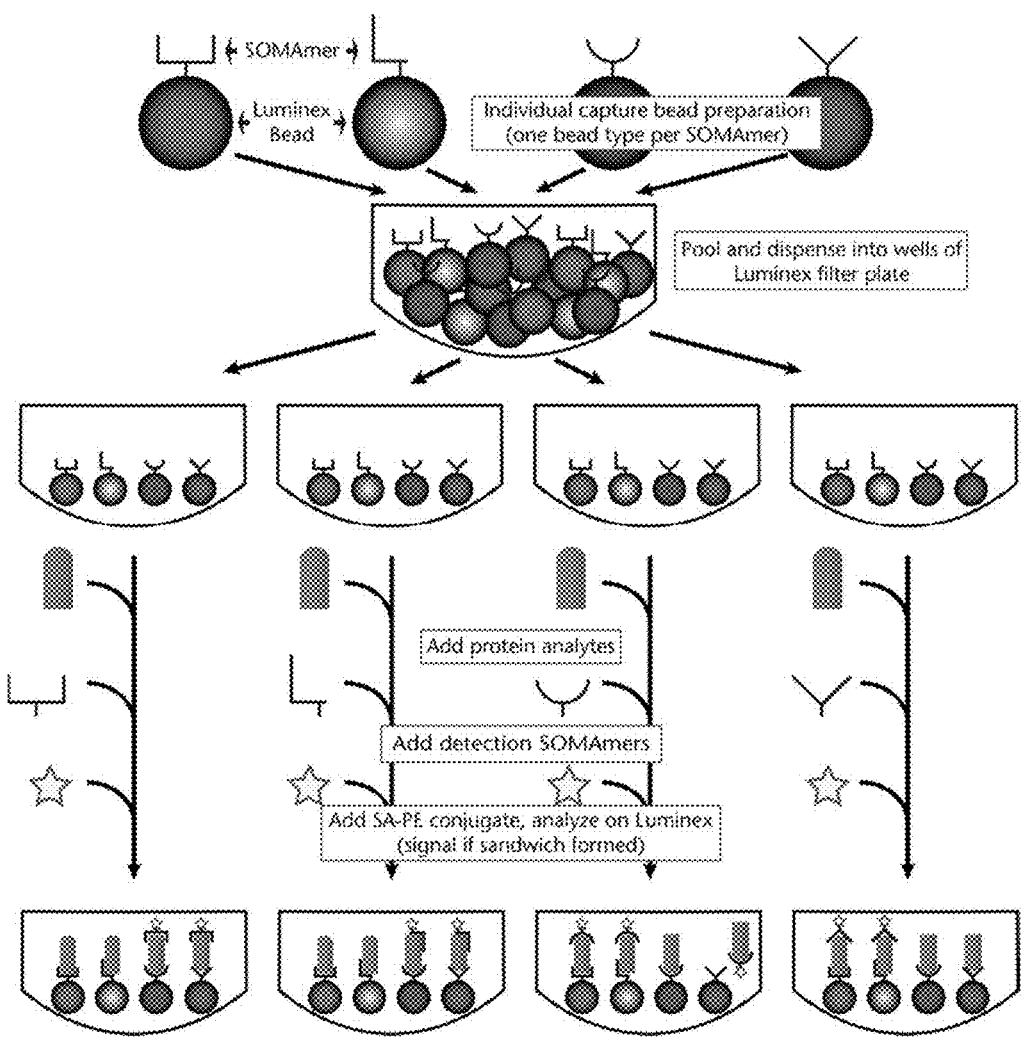
FIG. 2B shows a multiplexed sandwich screening assay on the Luminex platform to distinguish competitive from non-competitive binding. Each aptamer was immobilized on a different LumAvidin bead type, and capture beads were pooled for testing individual aptamers as detection agents.

While this binding assay was useful to identify aptamers that perform in sandwich format, it is limited to pair-wise testing. Thus, we set up a highly multiplexed sandwich screening assay method using the Luminex platform (FIG. 2B), as described in detail in Example 1.

Example 4: Selection of Aptamer Pairs for Target Proteins by a Modified Sandwich SELEX Method This example provides the representative method for the selection and production of DNA aptamer pairs for the following protein targets: matrix metalloproteinase-12 (MMP-12) and secreted phospholipase A2 (NPS-PLA2).

Aptamer pairs to the target proteins were obtained following a modified sandwich SELEX protocol that employed PBDC aptamers as capture agents attached on beads for partitioning of target-aptamer complexes, followed by photocleavage of the tripartite complexes. For MMP-12, the PBDC aptamer 4496-60 BndU was used to form a complex with the target for SELEX using a NapdU library. For NPS-PLA2, the PBDC aptamer 2692-74 BndU was used for complex formation in SELEX with a TrpdU library. After nine rounds of SELEX, the pools were sequenced and individual clones were prepared synthetically (AB-H 50mers) and tested for binding.

Table 28 provides a summary for the aptamers to the metalloproteinase-12 (MMP-12) protein. The nucleic acid molecule of clone 4496-60 is as an aptamer forty (40) nucleotides in length comprising C-5 modified pyrimidines, specifically BndU, and is capable of binding to the MMP-12 protein.

TABLE 28

MMP-12-4496-60 complex SELEX pool 12048 (NapdU mod.)
(n = 384 evaluable sequences)

| # | Clone ID | $K_d$ (nM) F.P. | $K_d$ (nM) w/Comp. | Sandwich |
|---|---|---|---|---|
| 9 | 12048-21 | 1.53 | NT | Yes |
| 8 | 12048-18 | 2.81 | NT | Yes |
| 7 | 12048-3 | 3.71 | NT | Yes |
| 7 | 12048-54 | 3.66 | NT | Yes |
| 4 | 12048-104 | 2.72 | NT | Yes |
| 3 | 12048-234 | 0.94 | NT | No |
| 346 | NT | NT | NT | NT |

NT, not tested

Table 29 provides a summary for the aptamers to the phospholipase A2 (NPS-PLA2) protein. The nucleic acid molecule of clone 2692-74, is as an aptamer forty (40) nucleotides in length comprising C-5 modified pyrimidines, specifically BndU, and is capable of binding to the NPS-PLA2 protein.

TABLE 29

NPS-PLA2-2692-74 complex SELEX pool 12055 (TrpdU mod.)
(n = 384 evaluable sequences)

| # | Clone ID | $K_d$ (nM) F.P. | $K_d$ (nM) w/Comp. | Sandwich |
|---|---|---|---|---|
| 12 | 12055-22 | 0.38 | NT | Yes |
| 372 | NT | NT | NT | NT |

NT, not tested

Example 5: Equilibrium Binding Constants of Aptamer Pairs

This example provides the representative method for measuring the equilibrium binding constants ($K_d$ values) for the DNA aptamer pairs.

Figure 2C:
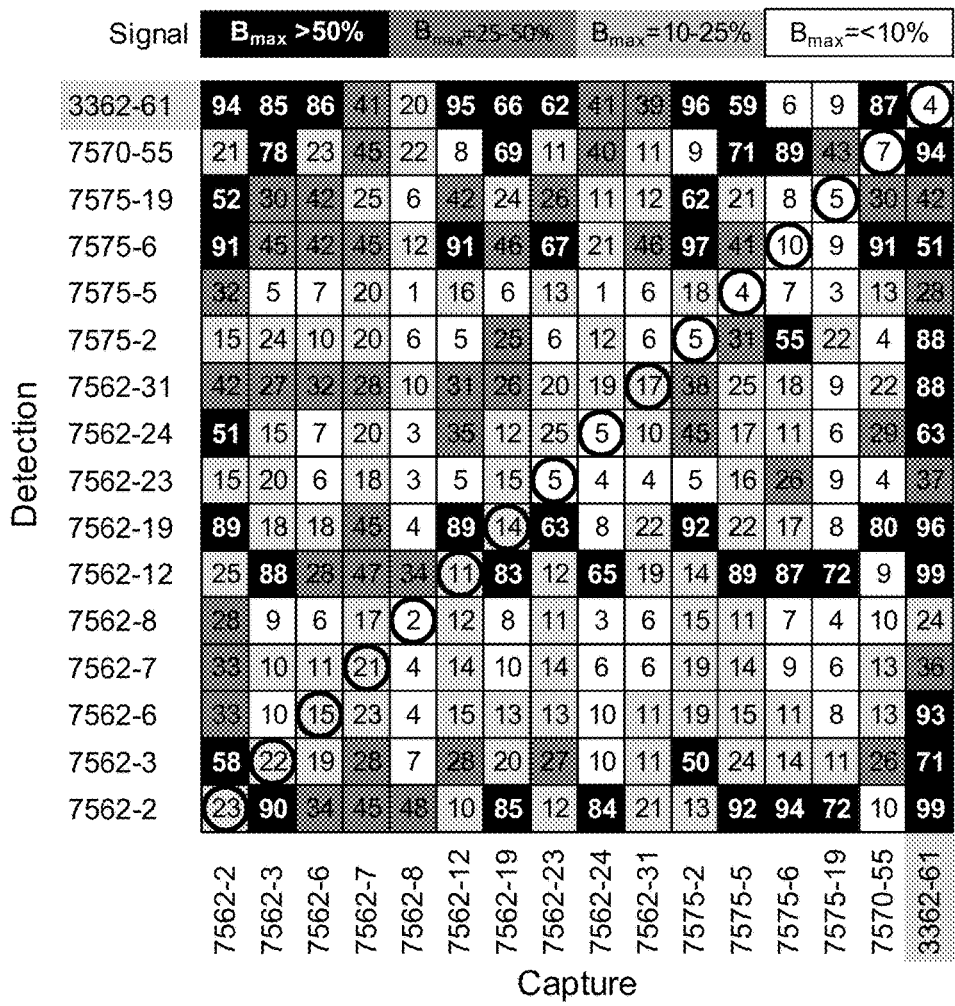
FIG. 2C shows pairwise screening of 16 CRDL1 aptamers in the Luminex-based multiplexed assay, with performance expressed as percent of maximum signal and displayed as heat map.

In brief, each of the clones for a given target was separately immobilized on a specific LumAvidin bead type. The beads were then pooled and used for capture of the target, and each of the sandwich candidate clones was used separately for detection. With respect to the number of aptamer sandwich candidates (ranging from 7-16 per target) for the eight panel proteins (ANGPT2, TSP2, CRDL1, MATN2, GPVI, ESAM, C7 and PLG), this approach reduced the two-dimensional matrix of pair-wise screening for functional aptamer sandwiches to one dimension, from 1116 assays ($15^2+14^2+16^2+14^2+9^2+7^2+8^2+7^2$) to 90 assays (15+14+16+14+9+7+8+7). The multiplexed Luminex sandwich screening assay allowed the rapid identification of functional aptamer pairs, e.g., by plotting the net signals as heat maps. For CRDL1 shown as an example in FIG. 2C, 16 aptamers were tested in a pair-wise matrix as capture and detection reagents, including 11 sequences containing TrpdU, 4 with 2NapdU, and the aptamer with BndU. The sandwich $K_d$ value improved by about 2.5 fold (comparing a BndU capture aptamer and BndU detection aptamer (2.19 nM $K_d$) with a BndU capture aptamer and TrpdU detection aptamer (0.88 nM $K_d$); see Table 30), and for C7, the sandwich $K_d$ value improved by about 6.3 fold (BndU capture aptamer and BndU detection aptamer (8.56 nM $K_d$) with a BndU capture aptamer and 2NapdU detection aptamer (1.35 nM $K_d$); see Table 30).

The Swiss Prot numbers for the proteins in Table 30 are as follows: ESAM (SwissProt # Q96AP7) and CdtA—binary toxin (SwissProt # Q9KH42), ANGPT2 (SwissProt #015123), TSP2 (SwissProt # P35442), CRDL1 (SwissProt # Q9BU40), MATN2 (SwissProt #000339), C7 (SwissProt # P10643), PLG (SwissProt # P00747), GPVI (SwissProt # Q9HCN6), MMP-12 (SwissProt #39900), NPS-PLA2 (SwissProt #14555).

TABLE 30

| Target Protein Name | Aptamer 1 (capture) | | | Aptamer 2 (detection) | | | Sandwich |
|---|---|---|---|---|---|---|---|
| | Clone ID | $K_d$ (nM) | Modified | Clone ID | $K_d$ (nM)[a] | Modified | $K_d$ (nM)[b] |
| ANGPT2[1] | 2602-2 | 0.07 | BndU | 7560-4 | 0.29 (0.59) | TrpdU | 1.90 |
| TSP2[1] | 3339-33 | 0.07 | BndU | 7574-53 | 0.08 (0.07) | 2NapdU | 0.02 |
| CRDL1[1] | 3362-61 | 1.05 | BndU | 7575-2 | 0.38 (0.19) | 2NapdU | 0.20 |
| MATN2[1] | 3325-2 | 0.14 | BndU | 7571-31 | 5.31 (3.65) | TrpdU | 0.88 |
| | | | | 3532-8[c] | 1.76 (0.94) | BndU | 2.19 |
| GPVI[1] | 3194-36 | 0.04 | BndU | 7564-5 | 0.04 (0.02) | TrpdU | 0.12 |
| ESAM[1] | 2981-9 | 0.25 | BndU | 7581-41 | 0.03 (0.06) | 2NapdU | >10 |
| C7[1] | 2888-49 | 2.71 | BndU | 7579-67 | 11.3 (0.13) | 2NapdU | 1.35 |
| | | | | 2888-68[c] | 2.08 (2.39) | BndU | 8.56 |
| PLG[1] | 4151-6 | 4.86 | BndU | 7567-64 | 13.1 (1.94) | TrpdU | 2.70 |
| | | | | 4151-5[c] | 2.00 (1.89) | BndU | 2.20 |
| CdtA[2] | 4758-6 | 0.86 | TrpdU | 5579-12 | 0.97 (0.28) | 2NapdU | 0.52 |
| MMP-12[1] | 4496-60 | 0.22 | BndU | 12048-54 | 3.66 (NT) | NapdU | 1.10 |
| NPS-PLA2[1] | 2692-74 | 0.02 | BndU | 12055-22 | 0.38 (NT) | TrpdU | 4.80 |

[1]Human protein;
[2]C. difficile protein
[a]Determined in radiolabel assay. Values in parentheses are for the complex of the target with aptamer 1
[b]Determined in Luminex bead-based sandwich assay
[c]Aptamer from archived sequences (without sandwich SELEX)

menu aptamer 3362-61 for CRDL1 performed well when used as a capture or as a detection agent in conjunction with any of the new clones. In contrast, clones 7575-6 and 7575-19 served better as detection agents (FIG. 2D). For comparison, sandwich assays using one of the new clones (7575-2) with any other new clone produced lower signals, and no pair was as good as the pair with the menu SOMAmer 3362-61 (FIG. 2E). No signals were obtained with the same SOMAmer used for capture and detection.

Figure 2F:
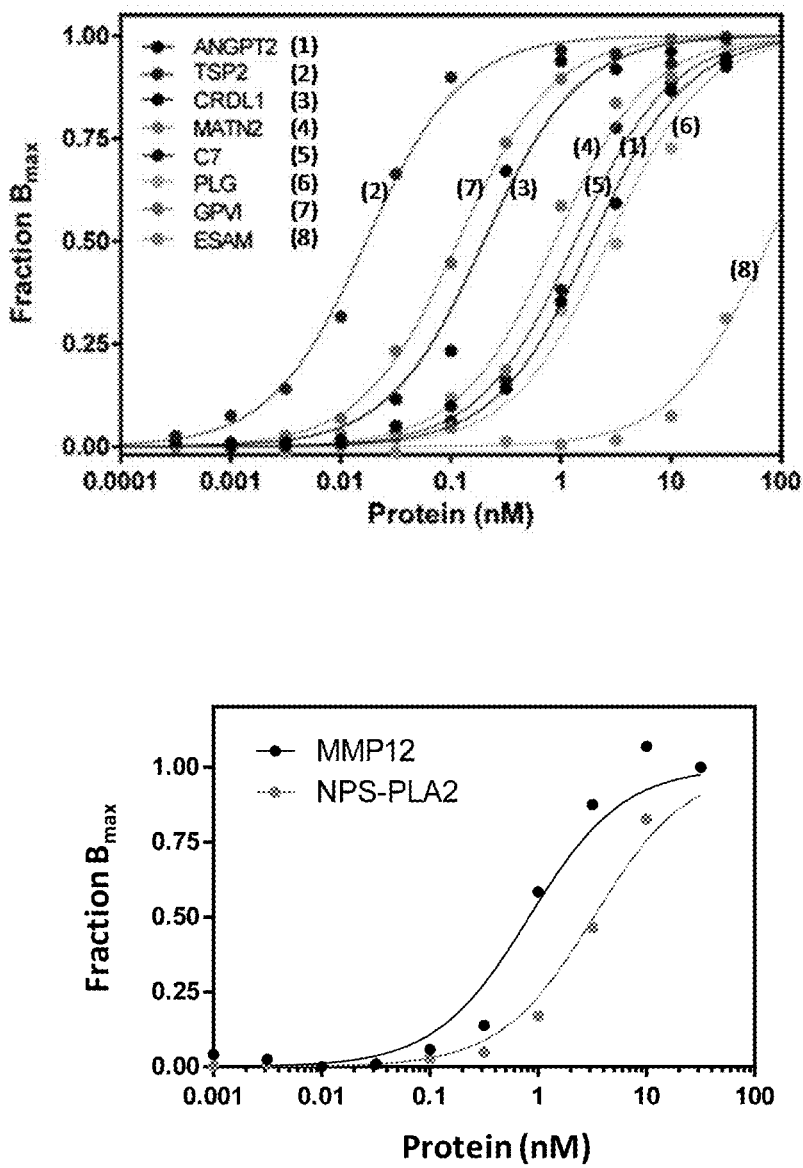
FIG. 2F shows sandwich binding curves obtained in the Luminex assay for proteins spiked in buffer (aptamers listed in Table 28). In all cases, the sequence that had served to form the complex with the target during the sandwich SELEX was used as the capture agent, and one of the new clones identified as a result of SELEX was used as the detection agent. The maximum signals (RFU at $B_{max}$) were 23046 (ANGPT2), 16623 (TSP2), 23349 (CRDL1), 25586 (MATN2), 26000 (C7), 13927 (GPVI), 7103 (PLG), and 3000 (ESAM), respectively.
Figure 3:
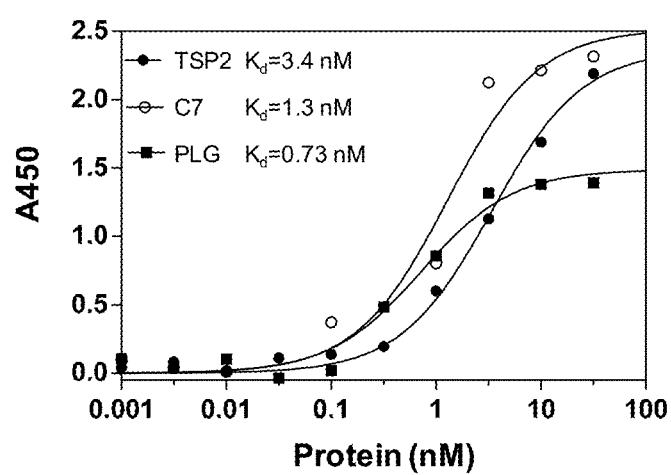
FIG. 3 shows the $K_d$ values for aptamer pairs used in a plate-based sandwich assay. Biotinylated aptamers were immobilized on streptavidin-coated plates as capture reagents, and used as detection agents for labelling with streptavidin-HRP conjugate.

Sandwich binding curves on the Luminex platform were generated for seven of the eight proteins: ANGPT2 (Angiopoietin-2), TSP2, CRDL1, MATN2, C7, PLG (Plasminogen), and GPVI, as well as, MMP-12 and NPS-PLA2 (FIG. 2F). The apparent equilibrium binding constants ($K_d$ values) of the new aptamers for the protein complexes with the cognate aptamer ranged from 0.02-2.7 nM (see Table 30). Of note, for the MATN2 and C7 sandwich assay, the "sandwich" $K_d$ values improved when the C-5 modified pyrimidine for the aptamer 1 (capture) and aptamer 2 (detection) were different. Specifically, for MATN2, the Besides the LumAvidin bead-based assay, we also evaluated some of the aptamer pairs in plate-based sandwich assays. With biotinylated aptamers as capture agents immobilized on streptavidin-coated plates, and as detection agents in conjunction with streptavidin-HRP conjugate, target titrations indicated differences in assay performance compared to the bead-based test. While the apparent $K_d$ value for the C7 aptamer pair was essentially identical in the two assay types, the TSP2 pair performed better in the Luminex assay, and the plasminogen pair somewhat better in the plate assay (see FIG. 3).

Tables 31 and 32 provide a summary of the physical and functional characteristics of the aptamers summarized in Table 30 that were used to make ternary complexes (i.e., "aptamer sandwiches"), and for the capture and detection of a target.

A description of the eleven (11) aptamers used as a "capture aptamer" (or first aptamer) is provided in Table 31.

TABLE 31

| Clone ID | Length (nts.) | C-5 Mod. | # of C-5 Mods. (% of 40-mer C.R.) | Base Composition of 40-mer Central Region (%) | | | Target Protein | $K_d$ (nM) |
|---|---|---|---|---|---|---|---|---|
| | | | | A | C | G | | |
| 2602-2 | 51 | BndU | 10 (25%) | 37.5% | 15.0% | 22.5% | ANGPT2[1] | 0.07 |
| 3339-33 | 51 | BndU | 9 (22.5%) | 20.0% | 30.0% | 27.5% | TSP2[1] | 0.07 |
| 3362-61 | 51 | BndU | 16 (40%) | 17.5% | 20.0% | 22.5% | CRDL1[1] | 1.05 |
| 3325-2 | 51 | BndU | 14 (35%) | 27.5% | 22.5% | 15.0% | MATN2[1] | 0.14 |
| 3194-36 | 51 | BndU | 11 (27.5%) | 20.0% | 17.5% | 35.0% | GPVI[1] | 0.04 |
| 2981-9 | 51 | BndU | 15 (37.5%) | 17.5% | 15.0% | 30.0% | ESAM[1] | 0.25 |
| 2888-49 | 58 | BndU | 16 (40%) | 17.5% | 20.0% | 22.5% | C7[1] | 2.71 |
| 4151-6 | 51 | BndU | 11 (27.5%) | 22.5% | 25.0% | 25.0% | PLG[1] | 4.86 |
| 4758-6 | 48 | TrpdU | 10 (25%) | 25.0% | 20.0% | 30.0% | CdtA[2] | 0.86 |
| 4496-60 | 50 | BndU | 9 (22.5%) | 25.0% | 25.0% | 27.5% | MMP-12[1] | 0.22 |
| 2692-74 | 50 | BndU | 17 (42.5%) | 25.0% | 15.0% | 17.5% | NPS-PLA2[1] | 0.86 |

"nts." is nucleotides
"Mod." is modification
"C.R." is central region of aptamer
[1]Human protein;
[2]C. difficile protein Generally, the aptamers that functioned as a "capture aptamer" (or first aptamer) were from about 48 to about 58 nucleotides in length (or from about 48, 49, 50, 51, 52, 53, 54, 55, 56, 57, or 58 nucleotides in length). Each aptamer comprised a 40-mer (40 nucleotides in length) central region (the remaining nucleotides of the aptamer flanked the 40-mer central region). The 40-mer central region comprises from about 9 to about 16 (or from 9, 10, 11, 12, 13, 14, 15 or 16) BndU or TrpdU C-5 modified pyrimidines. Alternatively, the 40-mer central region comprises from about 22% to about 40% (or from 22, 23, 24, 25, 26, 27, 28, 29, 30, 31, 32, 33, 34, 35, 36, 37, 38, 39 or 40%) BndU or TrpdU C-5 modified pyrimidines. Further, the 40-mer central region of the "capture aptamer" comprises from about 37% to about 58% GC content (or from about 37, 38, 39, 40, 41, 42, 43, 44, 45, 46, 47, 48, 49, 50, 51, 52, 53, 54, 55, 56, 57 or 58% GC content). The "capture aptamer" (or first aptamer) comprises a binding affinity for its target protein of from about 0.07 nM to about 4.9 nM (or from about 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8 or 4.9 nM).

A description of the fourteen (14) aptamers used as a "detection aptamer" (or second aptamer) is provided in Table 30.

TABLE 32

| Clone ID | Length (nts.) | C-5 Mod. | # of C-5 Mods. (% of 40-mer C.R.) | Base Composition of 40-mer Central Region (%) | | | Target Protein | $K_d$ (nM) |
|---|---|---|---|---|---|---|---|---|
| | | | | A | C | G | | |
| 7560-4 | 50 | TrpdU | 11 (27.5%) | 27.5% | 30.0% | 15.0% | ANGPT2[1] | 0.29 |
| 7574-53 | 50 | 2NapdU | 13 (32.5%) | 25.0% | 27.5% | 15.0% | TSP2[1] | 0.08 |
| 7575-2 | 50 | 2NapdU | 12 (30%) | 32.5% | 22.5% | 15.0% | CRDL1[1] | 0.38 |
| 7571-31 | 50 | TrpdU | 15 (37.5%) | 22.5% | 17.5% | 22.5% | MATN2[1] | 5.31 |
| 3532-8 | 58 | BndU | 13 (32.5%) | 20.0% | 20.0% | 27.5% | MATN2[1] | 1.76 |
| 7564-5 | 50 | TrpdU | 10 (25%) | 20.0% | 30.0% | 25.0% | GPVI[1] | 0.04 |
| 7581-41 | 50 | 2NapdU | 14 (35%) | 15.0% | 25.0% | 25.0% | ESAM[1] | 0.03 |
| 7579-67 | 50 | 2NapdU | 11 (27.5%) | 20.0% | 25.0% | 27.5% | C7[1] | 11.3 |
| 2888-68 | 58 | BndU | 11 (27.5%) | 15.0% | 20.0% | 37.5% | C7[1] | 2.08 |
| 7567-64 | 50 | TrpdU | 15 (37.5%) | 7.5% | 37.5% | 17.5% | PLG[1] | 13.1 |
| 4151-5 | 58 | BndU | 14 (35%) | 25.0% | 25.0% | 15.0% | PLG[1] | 2.00 |
| 5579-12 | 50 | 2NapdU | 9 (22.5%) | 35.0% | 20.0% | 22.5% | CdtA[2] | 0.97 |
| 12048-54 | 50 | NapdU | 5 (12.5%) | 32.5% | 20.0% | 35.0% | MMP-12[1] | 3.66 |
| 12055-22 | 50 | TrpdU | 11 (27.5%) | 25% | 25% | 22.5% | NPS-PLA2[1] | 0.38 |

"nts." is nucleotides
"Mod." is modification
"C.R." is central region of aptamer
[1]Human protein;
[2]C. difficile protein Generally, the aptamers that functioned as a "detection aptamer" (or second aptamer) were from about 50 to about 58 nucleotides in length (or from about 50, 51, 52, 53, 54, 55, 56, 57 or 58 nucleotides in length). Each aptamer comprised a 40-mer (40 nucleotides in length) central region (the remaining nucleotides of the aptamer flanked the 40-mer central region). The 40-mer central region comprises from about 5 to about 15 (or from 5, 6, 7, 8, 9, 10, 11, 12, 13, 14 or 15) BndU, TrpdU, NapdU or 2NapdU C-5 modified pyrimidines. Alternatively, the 40-mer central region comprises from about 12% to about 38% (or from 12, 13, 14, 15, 16, 17, 18, 19, 20, 21, 22, 23, 24, 25, 26, 27, 28, 29, 30, 31, 32, 33, 34, 35, 36, 37 or 38%) BndU, TrpdU, NapdU or 2NapdU C-5 modified pyrimidines. Further, the 40-mer central region of the "detection aptamer" (or second aptamer) comprises from about 37% to about 58% GC content (or from about 37, 38, 39, 40, 41, 42, 43, 44, 45, 46, 47, 48, 49, 50, 51, 52, 53, 54, 55, 56, 57 or 58% GC content). The "detection aptamer" (or second aptamer) comprises a binding affinity for its target protein of from about 0.03 nM to about 13.1 nM (or from about 0.3, 0.35, 0.4, 0.45, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.2, 10.4, 10.6, 10.8, 11, 11.2, 11.4, 11.6, 11.8, 12, 12.2, 12.4, 12.6, 12.8, 13, 13.2, 13.4, 13.6, 13.8 or 14 nM).

In summary, functional aptamer pairs suitable for sandwich assays of protein analytes were identified. Mining existing aptamers from archived SELEX pools, combined with an approach of applying a second SELEX with target-aptamer complexes support the notion that the use of different types of modified nucleotides enable for the identification of aptamer pairs capable of binding a target. In aptamer sandwich assays, background due to non-specific binding is reduced as a consequence of differential off-rates between specific and non-specific aptamers. This feature, combined with the added specificity inherent in two-reagent sandwich-type measurements, provides the basis for the development of assays with greater specificity and higher multiplexing abilities. Aptamers pairs hold promise toward the development of specific panels in various areas of medical diagnostics for which a large installed base of instruments is already in place.

REFERENCES

Zichi, D., Eaton, B., Singer, B. & Gold, L. Proteomics and diagnostics: Let's Get Specific, again. Curr Opin Chem Biol 12, 78-85 (2008).

Gold, L. et al. Aptamer-based multiplexed proteomic technology for biomarker discovery. PLoS One 5, e15004 (2010).

Gupta, S. et al. Rapid histochemistry using slow off-rate modified aptamers with anionic competition. Appl Immunohistochem Mol Morphol 19, 273-8 (2011).

Ochsner, U. A., Katilius, E. & Janjic, N. Detection of Clostridium difficile toxins A, B and binary toxin with slow off-rate modified aptamers. Diagn Microbiol Infect Dis (2013).

Pultar, J., Sauer, U., Domnanich, P. & Preininger, C. Aptamer-antibody on-chip sandwich immunoassay for detection of CRP in spiked serum. Biosens Bioelectron 24, 1456-61 (2009).

Ferreira, C. S. et al. DNA aptamers against the MUC1 tumour marker: design of aptamer-antibody sandwich ELISA for the early diagnosis of epithelial tumours. Anal Bioanal Chem 390, 1039-50 (2008).

Tasset, D. M., Kubik, M. F. & Steiner, W. Oligonucleotide inhibitors of human thrombin that bind distinct epitopes. J Mol Biol 272, 688-98 (1997).

Gong, Q. et al. Selection strategy to generate aptamer pairs that bind to distinct sites on protein targets. Anal Chem 84, 5365-71 (2012).

Shi, H., Fan, X., Sevilimedu, A. & Lis, J. T. RNA aptamers directed to discrete functional sites on a single protein structural domain. Proc Natl Acad Sci USA 104, 3742-6 (2007).

Xiao, S. J. et al. Sensitive discrimination and detection of prion disease-associated isoform with a dual-aptamer strategy by developing a sandwich structure of magnetic microparticles and quantum dots. Anal Chem 82, 9736-42 (2010).

Nonaka, Y., Sode, K. & Ikebukuro, K. Screening and improvement of an anti-VEGF DNA aptamer. Molecules 15, 215-25 (2010).

Sosic, A., Meneghello, A., Cretaio, E. & Gatto, B. Human thrombin detection through a sandwich aptamer microarray: interaction analysis in solution and in solid phase. Sensors (Basel) 11, 9426-41 (2011).

Huang, D. W., Niu, C. G., Qin, P. Z., Ruan, M. & Zeng, G. M. Time-resolved fluorescence aptamer-based sandwich assay for thrombin detection. Talanta 83, 185-9 (2010).

Tennico, Y. H., Hutanu, D., Koesdjojo, M. T., Bartel, C. M. & Remcho, V. T. On-chip aptamer-based sandwich assay for thrombin detection employing magnetic beads and quantum dots. Anal Chem 82, 5591-7 (2010).

Gold, L., Walker, J. J., Wilcox, S. K. & Williams, S. Advances in human proteomics at high scale with the SOMAscan proteomics platform. N Biotechnol 29, 543-9 (2012).

Baird, G. S. et al. Age-dependent changes in the cerebrospinal fluid proteome by slow off-rate modified aptamer array. Am J Pathol 180, 446-56 (2012).

De Groote, M. A. et al. Elucidating novel serum biomarkers associated with pulmonary tuberculosis treatment. PLoS One 8, e61002 (2013).

Ostroff, R. M. et al. Unlocking biomarker discovery: large scale application of aptamer proteomic technology for early detection of lung cancer. PLoS One 5, e15003 (2010).

Ostroff, R. M. et al. Early detection of malignant pleural mesothelioma in asbestos-exposed individuals with a noninvasive proteomics-based surveillance tool. PLoS One 7, e46091 (2012).

Mehan, M. R. et al. Protein signature of lung cancer tissues. PLoS One 7, e35157 (2012).

Mehan, M. R. et al. Highly multiplexed proteomic platform for biomarker discovery, diagnostics, and therapeutics. Adv Exp Med Biol 734, 283-300 (2013).

Vaught, J. D. et al. Expanding the chemistry of DNA for in vitro selection. J Am Chem Soc 132, 4141-51 (2010).

Brody, E. N. & Gold, L. Aptamers as therapeutic and diagnostic agents. J Biotechnol 74, 5-13 (2000).

Gold, L. Oligonucleotides as research, diagnostic, and therapeutic agents. J Biol Chem 270, 13581-4 (1995).

Kraemer, S. et al. From SOMAmer-based biomarker discovery to diagnostic and clinical applications: a SOMAmer-based, streamlined multiplex proteomic assay. PLoS One 6, e26332 (2011).

Perlee, L. et al. Development and standardization of multiplexed antibody microarrays for use in quantitative proteomics. Proteome Sci 2, 9 (2004).

Brody, E. N., Gold, L., Lawn, R. M., Walker, J. J. & Zichi, D. High-content affinity-based proteomics: unlocking protein biomarker discovery. Expert Rev Mol Diagn 10, 1013-22 (2010).

Davies, D. R. et al. Unique motifs and hydrophobic interactions shape the binding of modified DNA ligands to protein targets. Proc Natl Acad Sci USA 109, 19971-6 (2012).

Gill, R. D. et al. Cardiovascular risk event prediction and uses thereof. PCT/US2012/058060 (SomaLogic, Inc., USA, 2012).

What is claimed is:

1. A method for detecting a target in a sample, the method comprising:
   a) contacting the sample with a first aptamer to form a mixture, wherein the first aptamer is capable of binding to the target to form a first complex;
   b) incubating the mixture under conditions that allow for the first complex to form;
   c) contacting the mixture with a second aptamer, wherein the second aptamer is capable of binding the first complex to form a second complex;
   d) incubating the mixture under conditions that allow for the second complex to form;
   e) detecting for the presence or absence of the first aptamer, the second aptamer, the target, the first complex or the second complex in the mixture, wherein the presence of the first aptamer, the second aptamer, the target, the first complex or the second complex indicates that the target is present in the sample; and
   wherein, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are different,
   further wherein the first C-5 pyrimidine modification scheme comprises a 5-(N-benzylcarboxyamide)-2'-deoxyuridine (BndU).

2. The method of claim 1, wherein the first aptamer has binding affinity for the target and not the second aptamer.

3. The method of claim 1, wherein the second aptamer has binding affinity for the target and not the first aptamer.

4. The method of claim 1, wherein the second aptamer has binding affinity for the first complex.

5. The method of claim 1, wherein the first aptamer binding region of the target and the second aptamer binding region of the target are different regions.

6. The method of claim 1, wherein the first aptamer and the second aptamer, independently, comprise RNA, DNA or a combination thereof.

7. The method of claim 1, wherein each uracil or thymine of the first aptamer is a 5-(N-benzylcarboxyamide)-2'-deoxyuridine (BndU).

8. The method of claim 1, wherein the second C-5 pyrimidine modification scheme comprises a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

9. The method of claim 1, wherein each uracil or thymine of the second aptamer is a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

10. The method of claim 1, wherein the first aptamer and the second aptamer, independently, are each from 20 to 100 nucleotides in length.

11. The method of claim 1, wherein the first aptamer and/or the second aptamer further comprise a detectable moiety.

12. The method of claim 11, wherein the detectable moiety is selected from the group consisting of a dye, a quantum dot, a radiolabel, an electrochemical functional group, an enzyme, an enzyme substrate, a ligand and a receptor.

13. The method of claim 1, wherein the target comprises a protein or a peptide.

14. The method of claim 13, wherein the target is a protein selected from the group consisting ANGPT2, TSP2, CRDL1, MATN2, GPVI, ESAM, C7, PLG, MMP-12, NPS-PLA2 and CdtA.

15. The method of claim 1, wherein the dissociation constant ($K_d$) for the second complex is at least 0.02 nM, or from about 0.01 nM to about 10 nM, or from about 0.02 nM to about 6 nM, or from about 0.02 nM to about 3 nM.

16. The method of claim 1, wherein the dissociation constant ($K_d$) for the first complex is from about 0.04 nM to about 5 nM, or from about 0.04 nM to about 4.8 nM.

17. The method of claim 1, wherein the dissociation constant ($K_d$) for the second aptamer and the target is from about 0.03 nM to about 14 nM.

18. A method comprising:
  a) contacting a target with a first aptamer to form a mixture, wherein the first aptamer is capable of binding the target to form a first complex;
  b) incubating the mixture under conditions that allow for the first complex to form;
  c) contacting the mixture with a second aptamer, wherein the second aptamer is capable of binding the target to form a second complex;
  d) incubating the mixture under conditions that allow for the second complex to form;
  e) detecting for the presence or absence of the first aptamer and the second aptamer in the mixture, wherein the presence of both the first aptamer and second aptamer in the mixture indicates that the binding of the first aptamer to the target and the binding of the second aptamer to the target is non-competitive; and
  wherein, the first aptamer comprises a first C-5 pyrimidine modification scheme, the second aptamer comprises a second C-5 pyrimidine modification scheme, and wherein the first C-5 pyrimidine modification scheme and the second C-5 pyrimidine modification scheme are different.

19. The method of claim 18, wherein the first aptamer has binding affinity for the target and not the second aptamer.

20. The method of claim 18, wherein the second aptamer has binding affinity for the target and not the first aptamer.

21. The method of claim 18, wherein the second aptamer has binding affinity for the first complex.

22. The method of claim 18, wherein the first aptamer binding region of the target and the second aptamer binding region of the target are different regions.

23. The method of claim 18, wherein the first aptamer and the second aptamer, independently, comprise RNA, DNA or a combination thereof.

24. The method of claim 18, wherein each uracil or thymine of the first aptamer is a 5-(N-benzylcarboxamide)-2'-deoxyuridine (BndU).

25. The method of claim 18, wherein the second C-5 pyrimidine modification scheme comprises a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

26. The method of claim 18, wherein each uracil or thymine of the second aptamer is a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

27. The method of claim 18, wherein the first aptamer and the second aptamer, independently, are each from 20 to 100 nucleotides in length.

28. The method of claim 18, wherein the first aptamer and/or the second aptamer further comprise a detectable moiety.

29. The method of claim 28, wherein the detectable moiety is selected from the group consisting of a dye, a quantum dot, a radiolabel, an electrochemical functional group, an enzyme, an enzyme substrate, a ligand and a receptor.

30. The method of claim 18, wherein the target comprises a protein or a peptide.

31. The method of claim 30, wherein the target is a protein selected from the group consisting ANGPT2, TSP2, CRDL1, MATN2, GPVI, ESAM, C7, PLG, MMP-12, NPS-PLA2 and CdtA.

32. The method of claim 18, wherein the dissociation constant ($K_d$) for the second complex is at least 0.02 nM, or from about 0.01 nM to about 10 nM, or from about 0.02 nM to about 6 nM, or from about 0.02 nM to about 3 nM.

33. The method of claim 18, wherein the dissociation constant ($K_d$) for the first complex is from about 0.04 nM to about 5 nM, or from about 0.04 nM to about 4.8 nM.

34. The method of claim 18, wherein the dissociation constant ($K_d$) for the second aptamer and the target is from about 0.03 nM to about 14 nM.

35. The method of claim 18, wherein the first C-5 pyrimidine modification scheme comprises a C-5 modified pyrimidine selected from the group consisting of 5-(N-tryptaminocarboxyamide)-2'-deoxyuridine (TrpdU), 5-[N-(1-naphthylmethyl)carboxyamide]-2'-deoxyuridine (NapdU), 5-[N-(2-naphthylmethyl)carboxyamide]-2'-deoxyuridine (2-NapdU), and a combination thereof.

* * * * *